(12) United States Patent
Erenburg et al.

(10) Patent No.: US 11,344,358 B2
(45) Date of Patent: May 31, 2022

(54) APPARATUS FOR SELECTIVE TREATMENT OF TISSUE

(71) Applicant: Avava, Inc., Waltham, MA (US)

(72) Inventors: Irina Erenburg, Milton, MA (US); Jayant Bhawalkar, Auburndale, MA (US); Charles Holland Dresser, Wayland, MA (US); Joseph Ting, Acton, MA (US)

(73) Assignee: Avava, Inc., Waltham, MA (US)

( * ) Notice: Subject to any disclaimer, the term of this patent is extended or adjusted under 35 U.S.C. 154(b) by 0 days.

(21) Appl. No.: 16/444,496

(22) Filed: Jun. 18, 2019

(65) Prior Publication Data

US 2019/0388134 A1     Dec. 26, 2019

Related U.S. Application Data

(60) Provisional application No. 62/688,855, filed on Jun. 22, 2018.

(51) Int. Cl.
*A61B 18/00* (2006.01)
*A61B 18/04* (2006.01)
(Continued)

(52) U.S. Cl.
CPC .......... *A61B 18/04* (2013.01); *A61K 41/0028* (2013.01); *A61K 41/0052* (2013.01);
(Continued)

(58) Field of Classification Search
CPC .................. A61B 18/04; A61B 18/201; A61B 2018/00577; A61N 5/062; A61N 1/44;
(Continued)

(56) References Cited

U.S. PATENT DOCUMENTS 6,267,771 B1    7/2001  Tankovich et al.
6,287,549 B1 *  9/2001  Sumian ................ A61B 18/203
                                                                424/73
(Continued)

FOREIGN PATENT DOCUMENTS

EP          2556149 A1    2/2013
WO    2001/096619 A2    12/2001
(Continued)

OTHER PUBLICATIONS

International Search Report and Written Opinion of the International Searching Authority issued in corresponding International Application No. PCT/US2019/37719, dated Sep. 9, 2019, 10 pages.

(Continued)

*Primary Examiner* — Carl H Layno
*Assistant Examiner* — Anh-Khoa N Dinh
(74) *Attorney, Agent, or Firm* — Mintz Levin Cohn Ferris Glovsky and Popeo, P.C.

(57) ABSTRACT

A method includes depositing within a predetermined region of a target tissue with a plurality of dopant particles. The method also includes focusing a laser beam to a focal region that overlaps with at least a portion of the predetermined region. The focal region includes at least a first dopant particle of the plurality of dopant particles. The method further includes adjusting a first parameter of the laser beam to generate plasma within a plasma volume comprising the first dopant particle.

16 Claims, 16 Drawing Sheets
(7 of 16 Drawing Sheet(s) Filed in Color)

(51) Int. Cl.
*A61K 41/00* (2020.01)
*A61N 1/44* (2006.01)
*A61N 5/06* (2006.01)
*A61N 5/067* (2006.01)

(52) U.S. Cl.
CPC .... *A61N 5/062* (2013.01); *A61B 2018/00577* (2013.01); *A61N 1/44* (2013.01); *A61N 5/067* (2021.08); *A61N 2005/0626* (2013.01)

(58) Field of Classification Search
CPC ...... A61N 2005/067; A61N 2005/0626; A61K 41/0052; A61K 41/0028
USPC .................................................... 607/50, 51
See application file for complete search history.

(56) References Cited

U.S. PATENT DOCUMENTS

| | | | |
|---|---|---|---|
| 6,315,772 B1 * | 11/2001 | Marchitto | A61B 5/150099 606/9 |
| 6,670,576 B2 | 12/2003 | Troitski et al. | |
| 7,549,985 B2 | 6/2009 | O'Donnell | |
| 7,681,301 B2 | 3/2010 | Rodgers | |
| 8,496,579 B2 * | 7/2013 | Koenig | A61B 1/00172 600/160 |
| 8,523,926 B2 | 9/2013 | Neev | |
| 8,580,337 B2 | 11/2013 | Sjong | |
| 9,211,214 B2 * | 12/2015 | Rubinchik | C12N 15/87 264/400 |
| 9,687,508 B2 | 6/2017 | Anderson et al. | |
| 2003/0216719 A1 | 11/2003 | Debenedictis et al. | |
| 2004/0040379 A1 * | 3/2004 | O'Donnell | G01N 29/2418 73/627 |
| 2004/0043081 A1 | 3/2004 | Ye et al. | |
| 2005/0254282 A1 | 11/2005 | Summerfelt et al. | |
| 2009/0208580 A1 | 8/2009 | Shi et al. | |
| 2012/0197114 A1 | 8/2012 | Emelianov et al. | |
| 2013/0113140 A1 * | 5/2013 | Gunn-Moore | C12N 15/87 264/400 |
| 2013/0216779 A1 | 8/2013 | Hofmeister et al. | |
| 2014/0263217 A1 | 9/2014 | Pacetti et al. | |
| 2015/0080863 A1 * | 3/2015 | Welches | A61F 9/00814 606/5 |
| 2015/0250650 A1 * | 9/2015 | Mosquera | A61F 9/00814 606/5 |
| 2016/0074116 A1 | 3/2016 | Varghese et al. | |
| 2016/0199132 A1 | 6/2016 | Anderson et al. | |
| 2017/0151330 A1 | 6/2017 | Harris et al. | |
| 2018/0021172 A1 | 1/2018 | Zheleznyak et al. | |

FOREIGN PATENT DOCUMENTS

| | | | |
|---|---|---|---|
| WO | 2004/020986 A1 | 3/2004 | |
| WO | 2004/025284 A1 | 3/2004 | |
| WO | 2015/131102 A1 | 9/2015 | |
| WO | WO-2017070637 A1 * | 4/2017 | ............... A61N 1/44 |

OTHER PUBLICATIONS

U.S. Appl. No. 62/438,818 titled "Method and Apparatus For Selective Treatment Of Biological Tissue," filed Dec. 22, 2017.
Extended European Search Report for EP Application No. 19823551, dated Jan. 25, 2022, 7 pages.

* cited by examiner

APPARATUS FOR SELECTIVE TREATMENT OF TISSUE

CROSS REFERENCE TO RELATED APPLICATIONS

The present application claims priority of U.S. Provisional Application Ser. No. 62/688,855 filed Jun. 22, 2018, entitled "SELECTIVE PLASMA GENERATION FOR TISSUE TREATMENT," which is hereby incorporated by reference in its entirety.

BACKGROUND

Various conditions can be treated with the application of light or optical energy of certain wavelengths. Many challenges exist in delivering the energy to the appropriate target structure (e.g., tissue such as the skin) without damaging tissue structures adjacent to the target structure. These challenges include delivery of energy at an appropriate wavelength with sufficient fluence, as well as the ability to effectively and efficiently scan the target structure with the light or optical energy.

A challenge in light-based treatment occurs where a tissue to be treated effectively transparent, or lacks an ability to absorb light. This challenge thus far has prevented those with generally pigmentless (e.g., lacking eumelanin) hair follicles (e.g. blonde hairs and gray hairs) from being treated with laser hair removal technology.

Additionally, those patients having a darker skin tone are in general underserved by light-based treatments, as the added melanin their epidermis absorbs the treatment light causing unwanted side effects.

SUMMARY

Fractional approaches have been developed that involve application of optical energy to small, discrete treatment locations on the skin that are separated by healthy tissue to facilitate healing. Accurately targeting the treatment locations (e.g., located in dermal layer) with desirable specificity while avoiding damage to healthy tissue around the treatment location (e.g., in the epidermal layer) can be challenging. This requires, for example, an optical system with high numerical aperture (NA) for focusing a laser beam to a treatment location. Additionally, the optical system should be able to scan the focused beam over large affected regions (e.g., several square centimeters). Therefore, it is desirable to develop an optical system that can have high numerical aperture, and is capable of scanning over large affected regions. Further, it can be desirable that the optical system can treat the affected region in a reasonable time duration (e.g., less than an hour). Furthermore, it can be desirable that the optical system includes an interface that can, for example, establish a robust contact with the treatment region, stabilize the treatment region, cool the treatment region, and the like.

Past attempts have been made to introduce a dopant to a non-pigmented area for selective thermolysis treatment with a laser. An example of this is introducing gold nano-shells into sebaceous glands and then treating with a laser for treatment of acne. This is described in U.S. Pat. No. 9,687,508 by R. Anderson. Additionally, it has been desirable to dope pigment free hair follicles, so that those with fair skin and hair may undergo laser hair removal. In addition, doping and treating tissue in this manner is limited to applications where the surrounding tissue has a much lower (near zero) absorbance of the laser wavelength when compared with the dopant. In situations where the surrounding tissue also absorbs the laser wavelength another method is required.

Many patients having darker skin tones are underserved by energy-based dermatological devices, which selectively treat a target, or chromophore. This is because their melanin-rich epidermis absorbs energy as well as most naturally occurring targets. And as a result, the untargeted tissue can be affected with the same intensity as the target. It is therefore desired that a technology will allow people having darker skin types to appreciate the advancements in doped selective treatment of tissue, such as hair removal. For example, by focusing a treatment laser at a high NA to a location in the dermis of a patient, the intensity of the laser in the epidermis is much less than at the focus in the dermis. Additionally, a dopant may be used that has a much higher absorptivity than melanin at the wavelength of the laser, such that more intense absorption of the laser occurs within the dopant instead of the melanin.

Light or optical energy of certain wavelengths can interact with and transfer optical energy to a target tissue. The transfer of optical energy from electromagnetic radiation (EMR) (e.g., a laser beam) can lead to plasma generation by one or more of ionization (e.g., multiphoton ionization), heating, laser induced optical breakdown (LIOB), and laser induced thermal breakdown (LITB) in the target tissue. The generated plasma can be used to treat target tissues. Adding a dopant to the target tissue can reduce a minimum laser intensity required for LIOB ("threshold LIOB intensity), and/or reduce a minimum laser intensity required for LITB ("threshold LITB intensity"). Lowering of LIOB/LITB threshold intensities for predetermined regions of the target tissue (e.g., regions of the target tissue where dopants have been added) can allow for selective plasma generation in the predetermined regions. Selective plasma generation can allow for selective treatment of the target tissue.

Accordingly, improved methods, systems, and devices for EMR-based (e.g., laser-based) selective tissue treatment are provided.

A method includes depositing within a predetermined region of a target tissue with a plurality of dopant particles. The method also includes focusing a laser beam to a focal region that overlaps with at least a portion of the predetermined region. The focal region includes at least a first dopant particle of the plurality of dopant particles. The method further includes adjusting a first parameter of the laser beam to generate plasma within a plasma volume comprising the first dopant particle.

In one implementation, the plasma is generated within the first dopant particle. In another implementation, the plasma is generated in the plasma volume via laser induced thermal breakdown (LITB) due to absorption of a portion of the laser beam by the first dopant particle. In yet another implementation, a maximum intensity of the laser beam in the focal region is below a LITB threshold value of the target tissue without the dopant particles.

In one implementation, adjusting a first parameter of the laser beam includes setting the maximum intensity of the laser beam to a value between the LITB threshold value of the target tissue without the dopant particles and the LITB threshold value of the target tissue with the dopant particles. In one implementation, the plasma is generated in the plasma volume via laser induced optical breakdown (LIOB) due to absorption of a portion of the laser beam by the first dopant particle. In one implementation, a maximum intensity of the laser beam in at the focal region is below a LITB threshold value of the target tissue without the dopant particles.

In one implementation, adjusting a first parameter of the laser beam includes setting the maximum intensity of the laser beam to a value between the LITB threshold value of the target tissue without the dopant particles and the LITB threshold value of the target tissue with the dopant particles. In another implementation, adjusting the first parameter of the laser beam includes adjusting one or more of a power, a pulse energy, and a wavelength of the laser beam. In yet another implementation, the plurality of dopant particle includes one or more of sodium chloride, silicon, silver nanoparticles, metal nanocomposites, dendritic molecules.

In one implementation, the method further includes scanning the focal region of the laser beam along a first path in the predetermined region. In another implementation, scanning the focal region along the first path is configured to one or more of destroy, obliterate, cavitate, ablate, denature, and devitalizes the target issue along the first path. In one implementation, the generated plasma includes a first plasma generated from the first dopant particle, and a second plasma generated from the target tissue.

In one implementation, the plurality of dopant particle are deposited in the predetermined region by at least injecting the plurality of dopant particles in the target tissue. In another implementation, the focal region has a numerical aperture of at least 0.3. In yet another implementation, the laser beam has a wavelength selected based upon at least one of scattering and absorption in the target tissue. In one implementation, the wavelength is between about 0.5 and about 2.0 micron.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Embodiments of the disclosure will be more fully understood from the following detailed description taken in conjunction with the accompanying drawings, in which.

Figure 1:
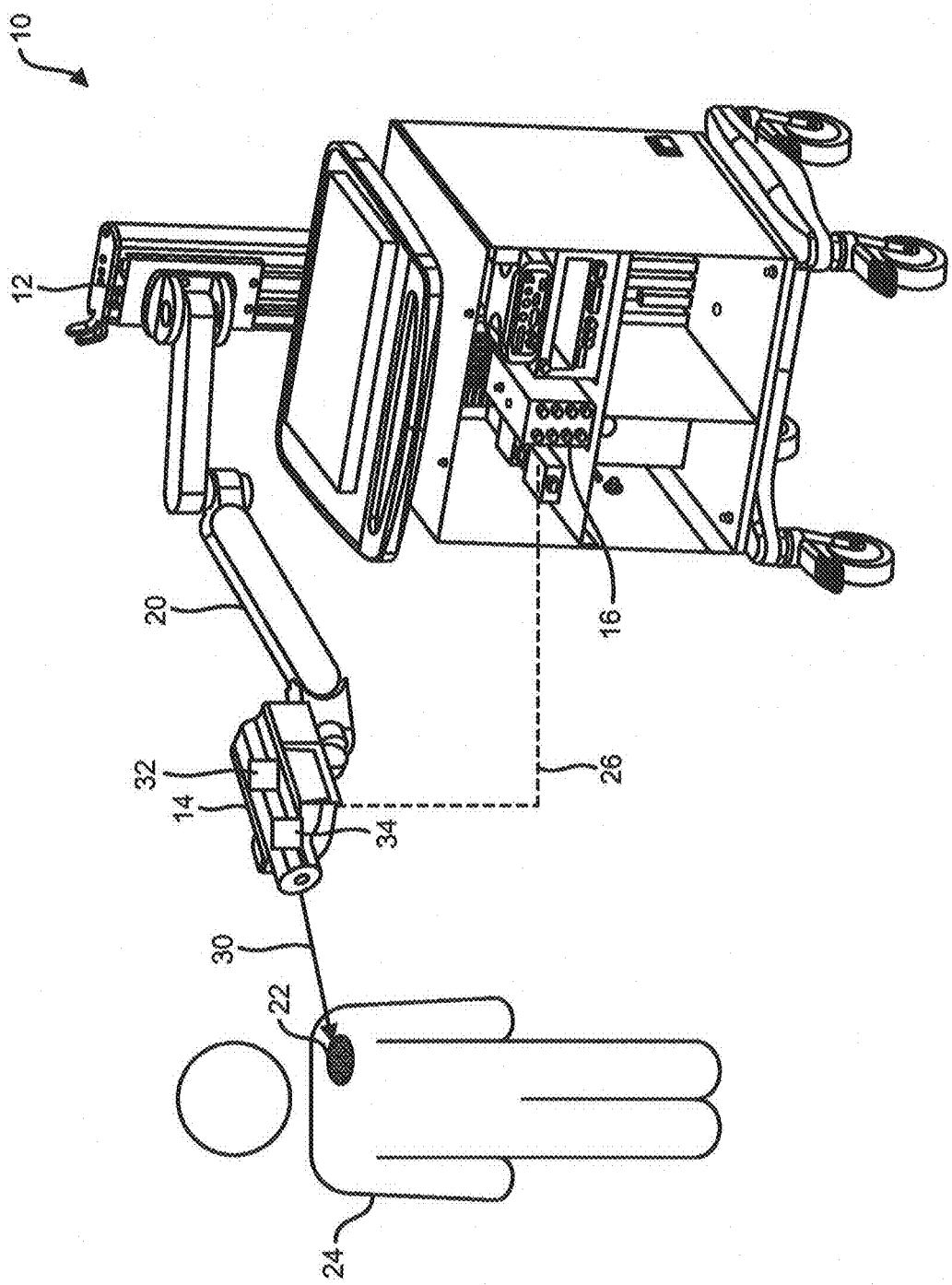
FIG. 1 illustrates an exemplary embodiment of a treatment system.

It is noted that the drawings are not necessarily to scale. The drawings are intended to depict only typical aspects of the subject matter disclosed herein, and therefore should not be considered as limiting the scope of the disclosure. Those skilled in the art will understand that the systems, devices, and methods specifically described herein and illustrated in the accompanying drawings are non-limiting exemplary embodiments and that the scope of the present invention is defined solely by the claims.

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Embodiments of the disclosure are discussed in detail below with respect to treatment of pigmentary conditions of the skin, such as melasma, to improve the appearance of such a pigmentary condition. However, the disclosed embodiments can be employed for treatment of other pigmentary and non-pigmentary conditions and other tissue and non-tissue targets without limit. Examples of pigmentary conditions can include, but are not limited to, post inflammatory hyperpigmentation, dark skin surrounding eyes, dark eyes, café au lait patches, Becker's nevi, Nevus of Ota, congenital melanocytic nevi, freckles/lentigo, hemosiderin rich structures, pigmented gallstones, lutein, zeaxanthin, rhodopsin, carotenoid, biliverdin, bilirubin and hemoglobin rich structures, and tattoo-containing tissue. Examples of non-pigmentary conditions can include, but are not limited to, hair follicles, hair shaft, vascular lesions, infectious conditions, sebaceous glands, acne, and the like.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

In general, high numerical aperture (NA) optical treatment systems are described that can focus electromagnetic radiation (EMR) (e.g., a laser beam) to a treatment region in a tissue. The focused laser beam can deliver optical energy to the treatment region without harming the surrounding tissue. The delivered optical energy can, for example, disrupt pigmented chromophores and/or targets in a treatment region of the dermal layer of the skin, without affecting the surrounding regions (e.g., overlying epidermal layer, other portions of the dermal layer, and the like) or within other pigmented target areas of the skin or tissue surrounded by unaffected and non-targeted areas. In other implementations, the delivered optical energy can cause tattoo removal or alteration, or hemoglobin-related treatment.

Exemplary methods and devices for treating skin conditions with light or optical energy are disclosed in U.S. Patent Application Publication No. 2016/0199132, entitled "Method and Apparatus for Treating Dermal Melasma," and U.S. Provisional Application No. 62/438,818, entitled "Method and Apparatus for Selective Treatment of Dermal Melasma," each of which is incorporated by reference herein in their entirety.

In general, systems and corresponding methods are provided for treatment of pigmentary conditions in tissues. As discussed in greater detail below, the disclosed systems and methods employ electromagnetic radiation (EMR), such as laser beams, to deliver predetermined amounts of energy to a target tissue. The EMR can be focused to a focal region and the focal region can be translated or rotated in any direction with respect to the target tissue. The predetermined amount of radiation can be configured to thermally disrupt or otherwise damage portions of the tissue exhibiting the pigmentary condition. In this manner, the predetermined amount of energy can be delivered to any position within the target tissue for treatment of the pigmentary condition such as to improve the appearance thereof.

FIG. 1 illustrates one exemplary embodiment of a treatment system 10. As shown, the treatment system 10 includes a mounting platform 12, and emitter 14, and a controller 16. The mounting platform 12 can include one or more manipulators or arms 20. The arms 20 can be coupled to the emitter 14 for performing various treatments on a target tissue 22 of a subject 24. Operation of the mounting platform 12 and emitter 14 can be directed by a user, manually or using the controller 16 (e.g., via a user interface). In certain embodiments (not shown), the emitter can have a hand-held form factor and the mounting platform 12 can be omitted. In other embodiments, the mounting platform can be a robotic platform and the arms can be communicatively coupled to the controller for manipulation of the emitter.

The emitter 14 and controller 16 (and optionally the mounting platform 12) can be in communication with one another via a communications link 26, which can be any suitable type of wired and/or wireless communications link carrying any suitable type of signal (e.g., electrical, optical, infrared, etc.) according to any suitable communications protocol.

Embodiments of the controller 16 can be configured to control operation of the emitter 14. In one aspect, the controller 16 can control movement of EMR 30. As discussed in detail below, the emitter 14 can include a source 32 for emission of the EMR 30 and a scanning system 34 for manipulation of the EMR 30. As an example, the scanning system 34 can be configured to focus EMR 30 to a focal region and translate and/or rotate this focal region in space. The controller 16 can send signals to the source 32, via the communications link 26 to command the source 32 to emit the EMR 30 having one or more selected properties, such as wavelength, power, repetition rate, pulse duration, pulse energy, focusing properties (e.g., focal volume, Raleigh length, etc.). In another aspect, the controller 16 can send signals to the scanning system 34, via the communications link 26 to command the scanning system 34 to move the focal region of the EMR 30 with respect the target tissue 22 in one or more translation and/or rotation operations.

As will be apparent from the description that follows, one advantageous aspect of the system described herein is that control of the treatment, by the controller 16 and/or the scanning system 34, enables a treatment pattern substantially in the form of a circle or overlapping circles. Thus, a feature of the system is to utilize a scanning pattern in the form of concentric circles rather than simply depositing a pattern of linear dots.

Embodiments of the treatment system 10 and methods are discussed herein in the context of targets within skin tissue, such as a dermal layer. However, the disclosed embodiments can be employed for treatment of any tissue in any location of a subject, without limit. Examples of non-skin tissues can include, but are not limited to, surface and sub-surface regions of mucosal tissues, genital tissues, internal organ tissues, and gastrointestinal tract tissues.

Figure 2:
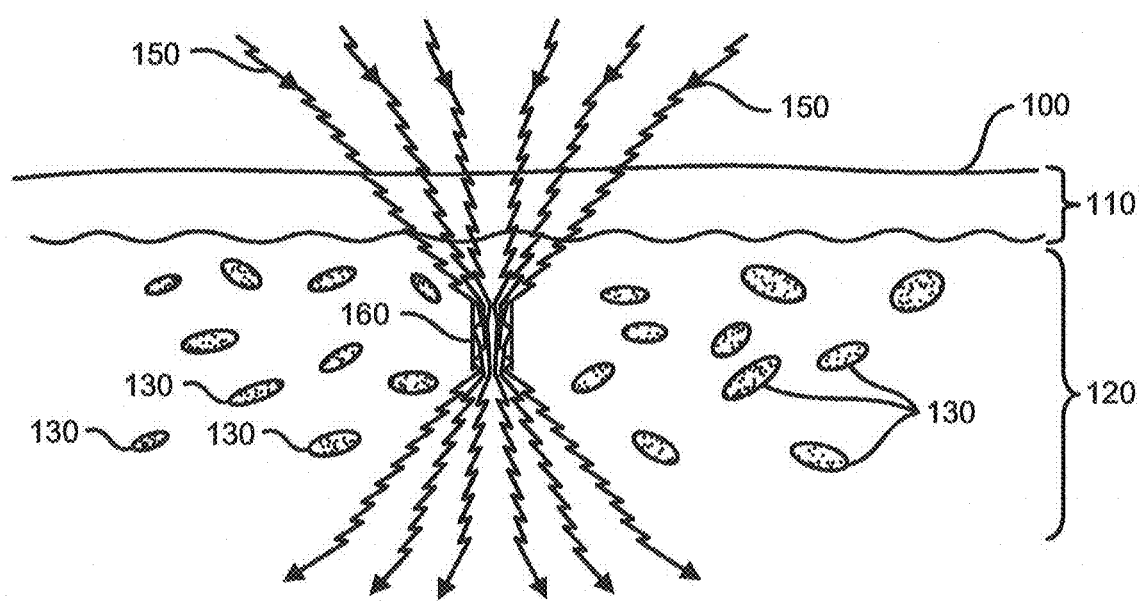
FIG. 2 is a schematic illustration of a laser beam focused into a pigmented region of a dermal layer in skin.

FIG. 2 is a schematic view of an illustration of a laser beam focused into a pigmented region of a dermal layer in a skin tissue. The skin tissue includes a skin surface 100 and an upper epidermal layer 110, or epidermis, which can be, e.g., about 60-120 µm thick in the facial region. The dermis can be slightly thicker in other parts of the body. For example, in general the thickness of the epidermis can range from about 30 µm (e.g., on the eyelids) to about 1500 µm (e.g., on the palm of the hand or soles of the feet). Such epidermis may be thinner or thicker than the examples above in certain conditions of the skin, for example psoriasis. The underlying dermal layer 120, or dermis, extends from below the epidermis 110 to the deeper subcutaneous fat layer (not shown). Skin exhibiting deep or dermal melasma can include a population of pigmented cells or regions 130 that contain excessive amounts of melanin. Electromagnetic radiation (EMR) 150 (e.g., a laser beam) can be focused into one or more focal regions 160 that can be located within the dermis 120, or the epidermis, 110. The EMR 150 can be provided at one or more appropriate wavelengths that can be absorbed by melanin. EMR wavelength(s) can be selected based on one or more criteria described below.

Properties of Treatment Radiation

Figures 3A, 3B:
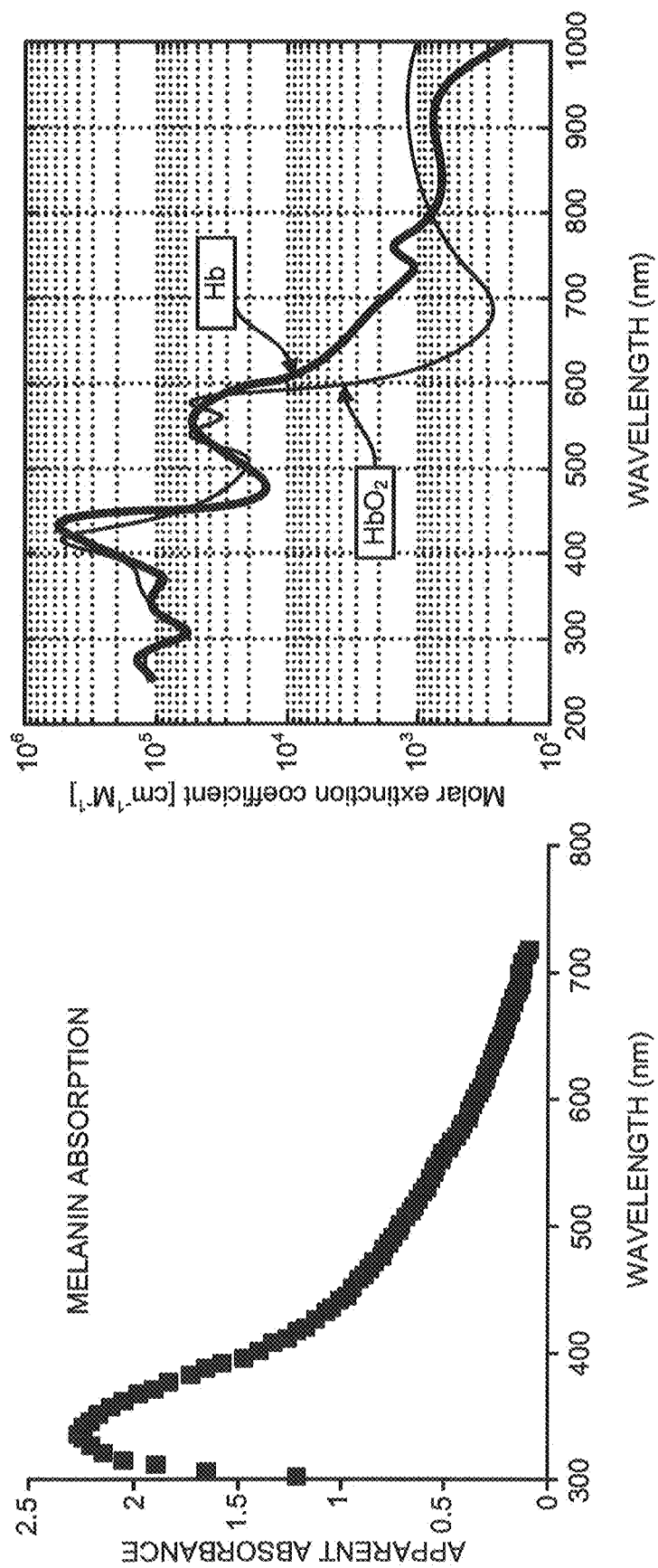
FIG. 3A is an exemplary absorbance spectrum graph for melanin.
FIG. 3B is an exemplary absorbance spectrum graph for hemoglobin.

Determination of desirable wavelength for treatment of certain skin conditions, such as pigmentary conditions and non-pigmentary conditions, can depend on, for example, the wavelength dependent absorption coefficient of the various competing chromophores (e.g., chromophore, hemoglobin, tattoo ink, etc.) present in the skin. FIG. 3A is an exemplary absorbance spectrum graph for melanin. The absorption of EMR by melanin is observed to reach a peak value at a wavelength of about 350 nm, and then decreases with increasing wavelength. Although absorption of the EMR by the melanin facilitates heating and/or disruption of the melanin-containing regions 130, a very high melanin absorbance can result in high absorption by pigment in the epidermis 110 and reduced penetration of the EMR into the dermis 120, or the epidermis 110. As illustrated in FIG. 3A, melanin absorption at EMR wavelengths that are less than about 500 nm are relatively high, such that wavelengths less than about 500 nm may not be suitable for penetrating sufficiently into the dermis 120 to heat and damage or disrupt pigmented regions 130 therein. Such enhanced absorption at smaller wavelengths can result in unwanted damage to the epidermis 110 and upper (superficial) portion of the dermis 120, with relatively little unabsorbed EMR passing through the tissue into the deeper portions of the dermis 120.

FIG. 3B is an exemplary absorbance spectrum graph for oxygenated or deoxygenated hemoglobin. Hemoglobin is present in blood vessels of skin tissue, and can be oxygenated ($HbO_2$) or deoxygenated (Hb). Each form of Hemoglobin may exhibit slightly different EMR absorption properties. As illustrated in FIG. 3B, exemplary absorption spectra for both Hb and $HbO_2$ indicate a high absorption coefficient for both Hb and $HbO_2$ at EMR wavelengths less than about 600 nm, with the absorbance decreasing significantly at higher wavelengths. Strong absorption of EMR directed into skin tissue by hemoglobin (Hb and/or $HbO_2$) can result in heating of the hemoglobin-containing blood vessels, resulting in unwanted damage to these vascular structures and less EMR available to be absorbed by the melanin.

Figure 4:
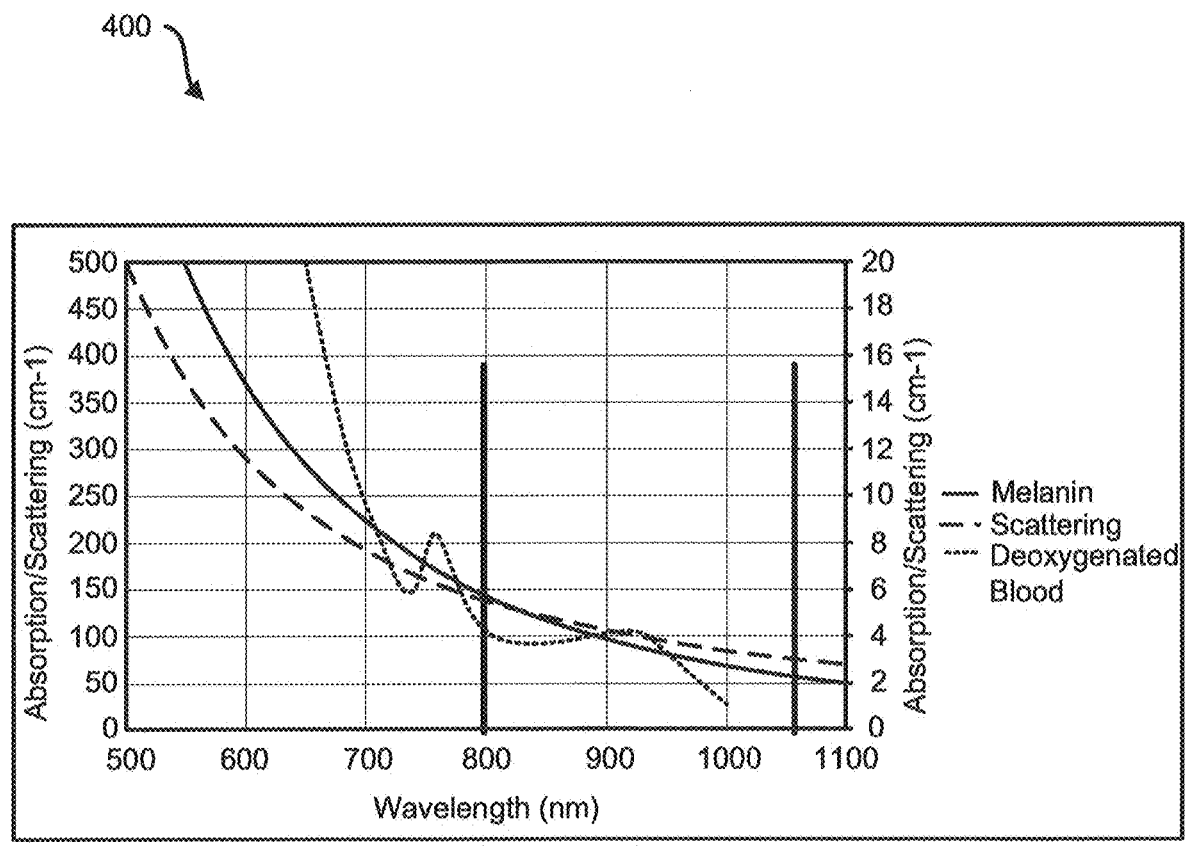
FIG. 4 illustrates a plot of the absorption coefficients of melanin and venous blood, and scattering coefficients of light in skin versus wavelength.

The choice of an appropriate wavelength for EMR can also depend on wavelength dependent scattering profile of tissues interacting with the EMR. FIG. 4 illustrates a plot of the absorption coefficient of melanin and venous blood versus wavelength. FIG. 4 also illustrates a plot of the scattering coefficient of light in skin versus wavelength. Absorption in melanin decreases monotonically with wavelength. If melanin is the target of a pigmentary condition treatment, a wavelength having a high absorption in melanin is desirable. This would suggest that the shorter the wavelength of light, the more efficient the treatment. However, absorption by blood increases at wavelengths shorter than 800 nm, thereby increasing the risk of unintentional targeting of blood vessels. In addition, as the intended target can be located below the skin surface, the role of scattering by skin (e.g., dermal layer) can be significant. Scattering reduces the amount of light that reaches the intended target. The scattering coefficient decreases monotonically with increasing wavelength. Therefore, while a shorter wavelength can favor absorption by melanin, a longer wavelength can favor deeper penetration due to reduced scattering. Similarly, longer wavelengths are better for sparing blood vessels due to a lower absorption by blood at longer wavelengths.

With the above considerations in mind, wavelengths can range from about 300 nm to about 3000 nm, and more particularly about 800 nm to about 1064 nm, can be used for targeting certain structures (e.g., melanin) in the dermis. In particular, wavelengths of about 800 nm and about 1064 nm can be useful for such treatments. The 800 nm wavelength can be attractive because laser diodes at this wavelength are less costly and readily available. However, 1064 nm can be particularly useful for targeting deeper lesions due to lower scattering at this wavelength. A wavelength of 1064 nm can also be more suitable for darker skin types in whom there is a large amount of epidermal melanin. In such individuals the higher absorption of lower wavelength EMR (e.g., about 800 nm) by melanin in the epidermis increases the chances of thermal injury to the skin. Hence, 1064 nm may be a more suitable wavelength of the treatment radiation for certain treatments for some individuals.

Various laser sources can be used for the generation of EMR. For example, Neodymium (Nd) containing laser sources are readily available that provide 1064 nm EMR. These laser sources can operate in a pulsed mode with repetition rates in a range of about 1 Hz to 100 kHz. Q-Switched Nd lasers sources may provide laser pulses having a pulse duration of less than one nanosecond. Other Nd laser sources may provide pulses having pulse durations more than one millisecond. An exemplary laser source providing 1060 nm wavelength EMR is a 20 W NuQ fiber laser from Nufern of East Granby, Conn., USA. The 20 W NuQ fiber laser provides pulses having a pulse duration of about 100 ns at a repetition rate in the range between about 20 kHz and about 100 kHz. Another laser source, is an Nd:YAG Q-smart 850 from Quantel of Les Ulis, France. The Q-smart 850 provides pulses having a pulse energy up to about 850 mJ and a pulse duration of about 6 ns at a repetition rate of up to about 10 Hz.

It can be desirable that the optical treatment system for treatment of tissues be capable of identifying treatment areas in a target tissue. (e.g., by imaging pigments, interface between dermal and epidermal layers in the target tissue). It can also be desirable to monitor/detect the interaction between EMR and the target tissue (e.g., plasma generation in tissue). Additionally, based on the detection, the optical treatment system can modify the treatment process (e.g., by changing intensity, size/location of focal region in the target tissue, etc.). Below, various embodiments of optical treatment systems are described.

A laser beam can interact with a tissue to generate a plasma within the tissue and this plasma can be used to treat the tissue. Plasma can be generated through a variety of mechanisms. Such mechanisms can include laser induced breakdown, such as laser induced optical breakdown (LIOB) and laser induced thermal breakdown (LITB).

In LIOB, a high intensity laser beam is applied to the tissue. Due to the high intensity of the laser beam, the atoms/molecules of the tissue can absorb multiple laser photons (e.g., via non-linear absorption) that can lead to ionization of electrons from the atoms/molecules and formation of the plasma.

Alternately, plasma can be generated via laser induced thermal breakdown (LITB). LITB is a thermo-physical process which is distinct from LIOB. LITB can be initiated by heating a target tissue by a laser beam. This can lead to ionization of the atoms/molecules of the target tissue to generate thermal electrons. The thermal electrons can rapidly re-combine with the ionized molecules from which they came. However, under appropriate conditions, the thermal electrons can also absorb incoming photons from the laser beam/EMR instead of recombining, resulting in thermionic plasma formation.

Thermionic plasma initiation can depend on the ability to liberate thermal electrons from atoms/molecules of the target tissue. Molecules having weakly-bound electrons are more likely to generate thermionic plasma when heated compared to molecules without weakly-bound electrons. Usually, the laser intensity needed for generating plasma via LIOB is higher than that for generating plasma via LITB (e.g., by several orders of magnitude).

Generation of plasma via LIOB and LITB can be enhanced in the presence of a dopant in the target tissue. In some implementations, the dopant (e.g., metal nanocomposites, dendrimers, any material containing an element having a low ionization energy (Sodium, Potassium), and any material having a low local work function where low ionization energy and local work function are low relative those properties in the target tissue etc.) can modify the electric field of the laser beam (e.g., in a region surrounding the dopant). This can reduce the laser intensity needed to generate plasma via LIOB. In other implementations, a dopant (e.g., a chromophore) can have a higher linear absorption than the ions/molecules of the surrounding target tissue. This can result in initiation of thermionic plasma formation (e.g., by linear absorption of laser photons, by heating, etc.) at lower laser intensities.

The efficacy of heating a dopant to initiate a thermionic plasma depends in part on energy density of the laser beam. The energy of a laser pulse in the laser beam is the time integral of laser power. Femto- and pico-second laser pulses, which can initiate dielectric breakdown in very short time intervals, tend to have an energy density that is below that needed for thermionic plasma initiation because of the very short duration of the pulses. Longer pulse durations, even those in the microsecond domain (a million times longer than the femtosecond domain), can initiate thermionic plasma formation under conditions where a suitable dopant is present and the local power density is sufficiently high. The pulse energy can be focused to a sufficient degree to provide a sufficiently high local energy density in the tissue.

Embodiments of systems and methods described herein can be configured to focus the EMR in a highly convergent beam. For example, one embodiment of the system can include a focusing or converging lens arrangement having a numerical aperture (NA) selected from about 0.3 to 0.9 (e.g., between about 0.5 and 0.9). The convergence angle of the EMR resulting from the NA can be relatively large, and it can provide a high fluence and intensity in the focal region of the lens, which can be located at a region inside the target tissue. Concurrently, a lower fluence can be present in the overlying portions of the target tissue located upstream from the focal region. Such focal geometry can help reduce unwanted heating and thermal damage in the overlying portions of the target tissue. The exemplary optical arrangement can further include a collimating lens arrangement configured to direct EMR from the emitting arrangement onto the focusing lens arrangement. The collimating lens arrangement can ensure that the EMR beam emerging from the laser arrangement has a uniform cross-section as it propagates (e.g., propagates through an optical system).

Embodiments of optical systems employed within the system can be configured to focus the EMR to a focal region of predetermined size. As an example, the focal region can possess a width or spot size that is less than about 200 am, for example, less than about 100 am, or even less than about 50 μm, e.g., as small as about 1 am. For example, the spot size can range from about 1 μm to about 50 μm, from about 50 μm to about 100 μm, and from about 100 μm to about 200 μm. The spot size of the focal region can be determined, for example, in air. Such spot size can be selected as a balance between being small enough to provide a high fluence or intensity of EMR in the focal region (e.g., to effectively irradiate pigmented structures in the dermis of a skin tissue, to effectively irradiate doped region of a target tissue, etc.), and being large enough to facilitate irradiation of large regions/volumes of the target tissue in a reasonable time. The exemplary optical arrangement can also be configured to direct the focal region of the EMR onto a location within the target tissue that is at a depth below the surface of the target tissue (e.g., dermal layer of a skin tissue), such as in the range from about 120 μm to about 1000 μm, e.g., between about 150 μm to about 300 μm.

Such exemplary depth ranges can correspond to typical observed depths of pigmented regions in skin that exhibits dermal melisma or other targets of interest. This focal depth can correspond to a distance from a lower surface of the apparatus configured to contact the skin surface and the location of the focal region. Additionally, some embodiments can be configured for treating targets within the epidermis. For example, an optical arrangement may be configured to direct a focal region of the EMR to a location within the epidermis tissue, for example in a range from about 5 μm to 2000 μm beneath the skin surface. Still other embodiments may be configured for treating a target deep in the dermis. For example, a tattoo artist typically calibrates his tattoo gun to penetrate the skin to a depth from about 1 mm to about 4 mm beneath the skin surface. Accordingly, in some embodiments an optical arrangement may be configured to direct a focal region of the EMR to a location within the dermis tissue in a range from about 0.4 mm to 4 mm beneath the skin surface.

In certain embodiments of the present disclosure, EMR at one or more wavelengths can be focused into the target tissue, such that the optical energy is selectively absorbed by regions of the target tissue containing dopants. In certain embodiments, the EMR can be pulsed and/or scanned. Such linear absorption of the optical energy can lead to local thermionic emission of electrons. With appropriate selection of optical energy parameters and beam geometry, further irradiation of the target tissue can lead to further energy absorption by the emitted electrons, followed by local plasma formation and non-linear absorption of energy. This procedure can produce intense heat, local expansion, stress waves such as strong acoustic or shockwaves, and/or chemical reactions due to the plasma in the dopant-containing region of target tissue.

In exemplary embodiments of the present disclosure, laser-induced plasma can be generated (e.g., via LIOB, LITB, etc.) in the focal region within the target tissue, based in part on selective absorption of the optical energy by dopants in the target tissue. Thermionic plasma formation requires a threshold level of power and energy density at the site where a dopant is present. According to some embodiments, the focal region within the target tissue can be scanned to initiate plasma formation at a depth defined by the laser focus geometry, and such plasma can be selectively formed only at sites where a dopant is present. In this manner, a focused, scanned laser can be used to selectively damage well-defined regions in the target tissue that contain dopants (e.g., within one or more focal planes).

The focal region size/width, quality, and length along the beam axis of a focused laser beam directed into a target tissue can be determined by factors such as one or more of the laser beam divergence, laser mode structure, numerical aperture of the beam focusing optics, aberrations of the focusing optics, coupling of the beam into tissue at the tissue surface (e.g. surface reflection and refraction effects), and optical scattering properties of the tissue.

As discussed herein, the term "Rayleigh range" can include its ordinary meaning as understood by one of skill in the art and it can be used to describe the extent or length of a focal region along the optical axis. For example, the Rayleigh range can describe the size of a focal region along the depth or z axis for a beam directed into target tissue. The Rayleigh range is affected by such factors, e.g., as the laser source divergence, wavelength of the optical energy, laser mode(s), original diameter of the beam prior to convergence by optical elements, and numerical aperture of the focusing system. For example, a highly-convergent beam, where the outer boundaries of the beam converge at a relatively large angle as the beam reaches the focal region (and diverge at a similar angle beyond the focal region), can exhibit relatively small Rayleigh length. A smaller focused convergence angle can lead to a larger Rayleigh range, as the beam converges and diverges slowly with respect to distance along the beam axis. Typically, the Rayleigh range is several times larger than the transverse focal spot diameter.

By varying the focusing optical design and/or laser mode structure, a wide variety of laser focal spots can be produced. These focal spots can be characterized by geometrical parameters such as spot size or width (e.g., a characteristic dimension perpendicular to the axis of the beam in the focal region), and the Rayleigh range (e.g., a dimension of the focal region along the longitudinal axis of the beam). The appropriate dimensions of a focal region for selectively initiating plasmas in target tissue (via thermionic emission) can be selected based on factors such as the size of the dopant being targeted, the pulse energy and power of the optical energy source (which, together with the size of the focal region will affect local power and energy densities), the Rayleigh range (which will further affect the range of depths that can be scanned within a volume of target tissue in a particular time interval), etc.

Exemplary embodiments of the present disclosure can provide devices and methods for selectively producing plasma in a desired (e.g., predetermined) portion of a target tissue (e.g., dermal layer) using a laser beam. This can be done, for example, by adding a dopant to a region of the target tissue ("doped region"). Addition of the dopant can reduce the threshold intensity of the laser beam required to generate plasma in the doped region (e.g., via LIOB, LITB, etc.). As a result, plasma can be generated in the doped region using a laser beam of lower intensity compared to a region of the target tissue that has not been doped (e.g., an undoped region). This can allow for selective plasma generation in the target tissue. For example, a laser beam having an intensity below a threshold intensity (e.g., LIOB threshold intensity for undoped region, LITB threshold intensity for undoped region, etc.) will generate a plasma when interacting with the doped region, and will not generate a plasma (or generate very little plasma) when interacting with the undoped region.

Figure 5:
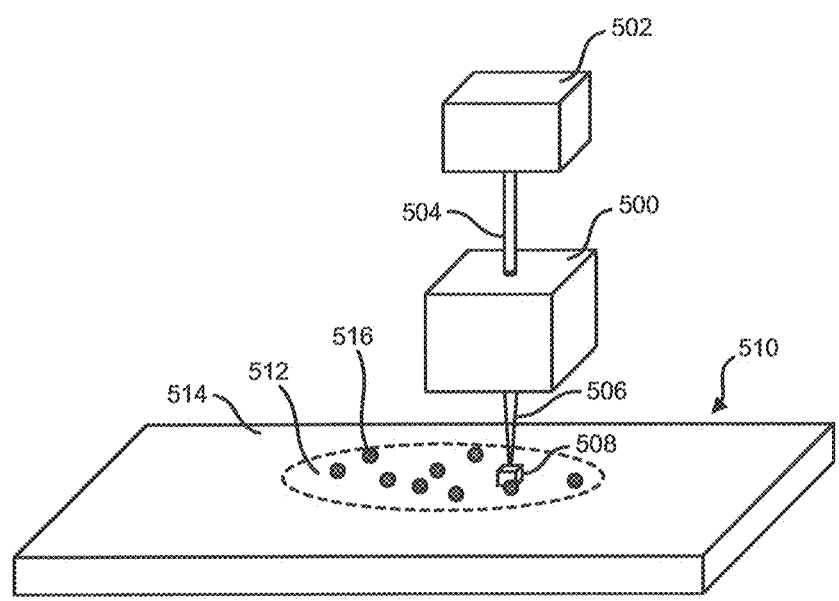
FIG. 5 is a schematic illustration of an exemplary optical system for selective plasma generation in a target material.
Figure 6:
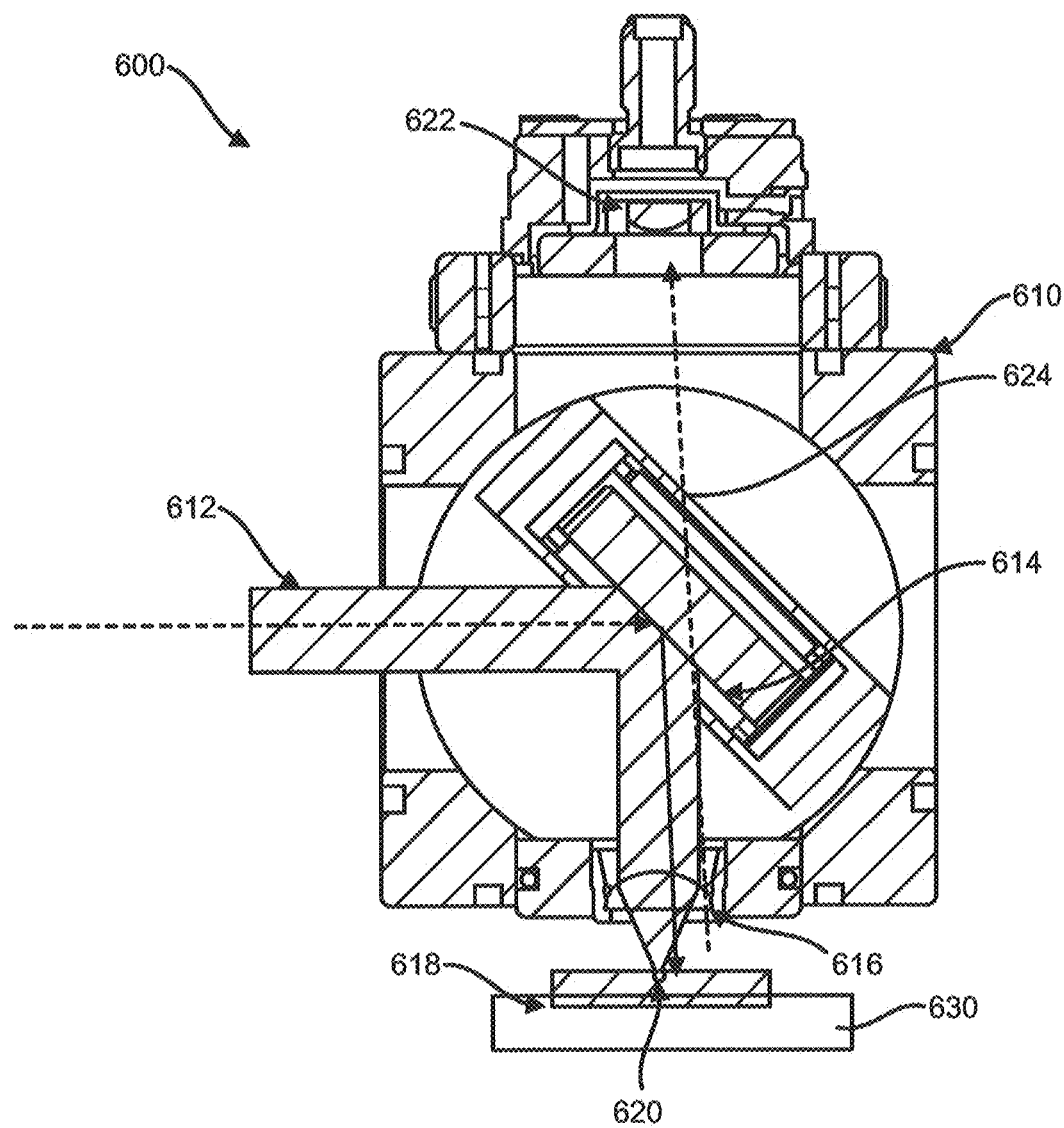
FIG. 6 is a schematic illustration of an exemplary optical system.

FIG. 5 is a schematic illustration of an exemplary optical system 500 configured to perform selective plasma generation in a target tissue (e.g., in a dermal layer of the target tissue). The optical system 500 can receive a laser beam 504 from a laser source 502. The optical system 500 includes an objective (not shown) that can focus the laser beam 504 and directs a focused laser beam 506 to a focal region 508 in the target tissue 510. The target tissue 510 can include a doped region 512 and an undoped region 514. The doped region can includes a plurality of dopants 516. The dopants 516 can be added to the target tissue 510 through diffusion from a tissue surface, diffusion through a fractionated laser treated surface of the tissue, through bodily systems (e.g., orally administered), and through tattoo. The dopants 516 can include, for example, silicon, silver nanoparticles, metal nanocomposites, dendritic molecules metal nanoparticles, dyes, and pigments.

As the objective moves (e.g., relative to the scanning system 500 and/or due to movement of the entire scanning system 500), the focal region can trace a path through/along the target tissue 510. For example, the focal region 508 can travel from the doped region 512 to the undoped region 514 or vice versa. The intensity of the focused laser beam 506 can be adjusted such that plasma is generated in the doped region, and not generated (or generated to a much smaller degree compared to the doped region) in the undoped region 514. The threshold LITB/LIOB intensity can be lower in the doped region compared to the undoped region. By adjusting the intensity of the focused laser beam 506 to a value between the threshold LITB intensity of the undoped region 514 and the threshold LITB intensity of the doped region 512, thermionic plasma can be selectively generated in the doped region 512. Similarly, by adjusting the intensity of the focused laser beam 506 to a value between the threshold LIOB intensity of the undoped region 514 and the threshold LIOB intensity of the doped region 512, plasma from optical breakdown can be selectively generated in the doped region 512. In some implementations, selective plasma generation (e.g., in the doped region) can be achieved by varying one or more of power, pulse energy, pulse duration, and wavelength of the focused laser beam 506.

Interaction between the focused laser beam 506 and the dopant 516 can lead to generation of plasma in and/or around the dopant 516 (e.g., in a volume surrounding the dopant 516). For example, plasma can be initiated by ionization of an electron from the dopant 516 by the focused laser beam 506, which in turn can cause ionization of other dopants and/or atoms (or molecules) of the target tissue 510. In some implementations, plasma can be generated in and/or around the dopant 516 by LIOB. The generated plasma (e.g., via LIOB, via LITB, etc.) can propagate in the target tissue (e.g., along the direction of propagation of the focused laser beam 506). The propagating plasma can ionized atoms/molecules of the target tissue (e.g., by electron impact dissociation).

Dopants can be added to a target tissue to achieve selective thermolysis treatment with a laser beam. For example, introducing gold nano-shells into sebaceous glands can allow for selective treatment of acne. This process has been described in U.S. Pat. No. 9,687,508 which has been incorporated herein in its entirety. In some implementations, doping pigment free hair follicles can allow individuals with fair skin to undergo laser hair removal. The aforementioned acne treatment and hair removal can be effectively implemented, for example, when the surrounding skin tissue does not absorb (or absorbs very little) the laser beam responsible for the thermolysis treatment (e.g., acne treatment, hair removal, etc.). Performing selective thermolysis treatment on patients of color can be challenging. This can be due to higher rate of EMR absorption by the melanin-rich skin tissue (e.g., epidermis of the skin tissue) surrounding the tissue target (e.g., acne, hair follicle, etc.). According to some embodiments, the use of a dopant and a converging laser beam addresses this challenge, as a laser intensity within the melanin rich epidermis is less than at a target region and absorption (or affinity for laser induced breakdown) at a target region is enhanced by a dopant.

is a schematic illustration of an exemplary optical system 600. The optical system 600 includes a beam combiner 610 configured to receive a collimated laser beam 612. The beam combiner 610 includes a reflector 614 that reflects the incident laser beam 612. The reflector 614 is selected to reflect light having a predetermined wavelength range. In the current study, the laser beam 612 has a wavelength of 1060 nm, and the reflector is a Thorlabs NB1-K14, which is 99.5% reflective over a wavelengths range of 1047 to 1064 nm. The reflected laser beam 612 is imaged and focused by a focus optic 616. The focus optic 616 used in this study is a Thorlabs C240TME-C, which is an aspheric lens capable of diffraction limited performance, and has an NA of 0.5 and an effective focal length of 8 mm. The laser beam 612 is focused to a waist (e.g., focal volume) in a target tissue 618 (a skin sample). At the waist of the laser beam 612, a plasma plume 620 is generated within the target tissue sample 618. Radiation 624 generated from the plasma plume 620 is imaged by the focus optic 616 and is transmitted through the reflector 614. After transmission through the reflector 614, radiation 624 is imaged into a first end of a fiber optic (not shown) by a fiber coupler, 622. The fiber coupler used in the study is a Thorlabs PAF-SMA-7-A. A second end of the fiber optic is coupled to a spectrometer (not shown) which is an Ocean Optics HR2000+ ES. In another implementation of the study, a notch filter (not shown) is included between the reflector 614 and the fiber coupler 622 to block portions of the radiation 624 having a wavelength similar to that of the laser beam 612 from entering the fiber optic. The target tissue 618, is mounted on motorized staging 630. A working distance between the target tissue 618, and the focus optic 616, is maintained to control a depth of the waist of the laser beam 612 within the target tissue 618.

The laser beam, 612, was provided by a laser source, specifically a 10 W Nufern Fiber laser. The laser was operated at 20 kHz, 100 nS pulse duration, and 0.5 mJ/pulse. The tissue was scanned during laser irradiation at a rate of 100 mm/S. The spectrometer was adjusted to capture light over a 5000 mS period and trigger capturing in response to the laser irradiation.

Figure 7:
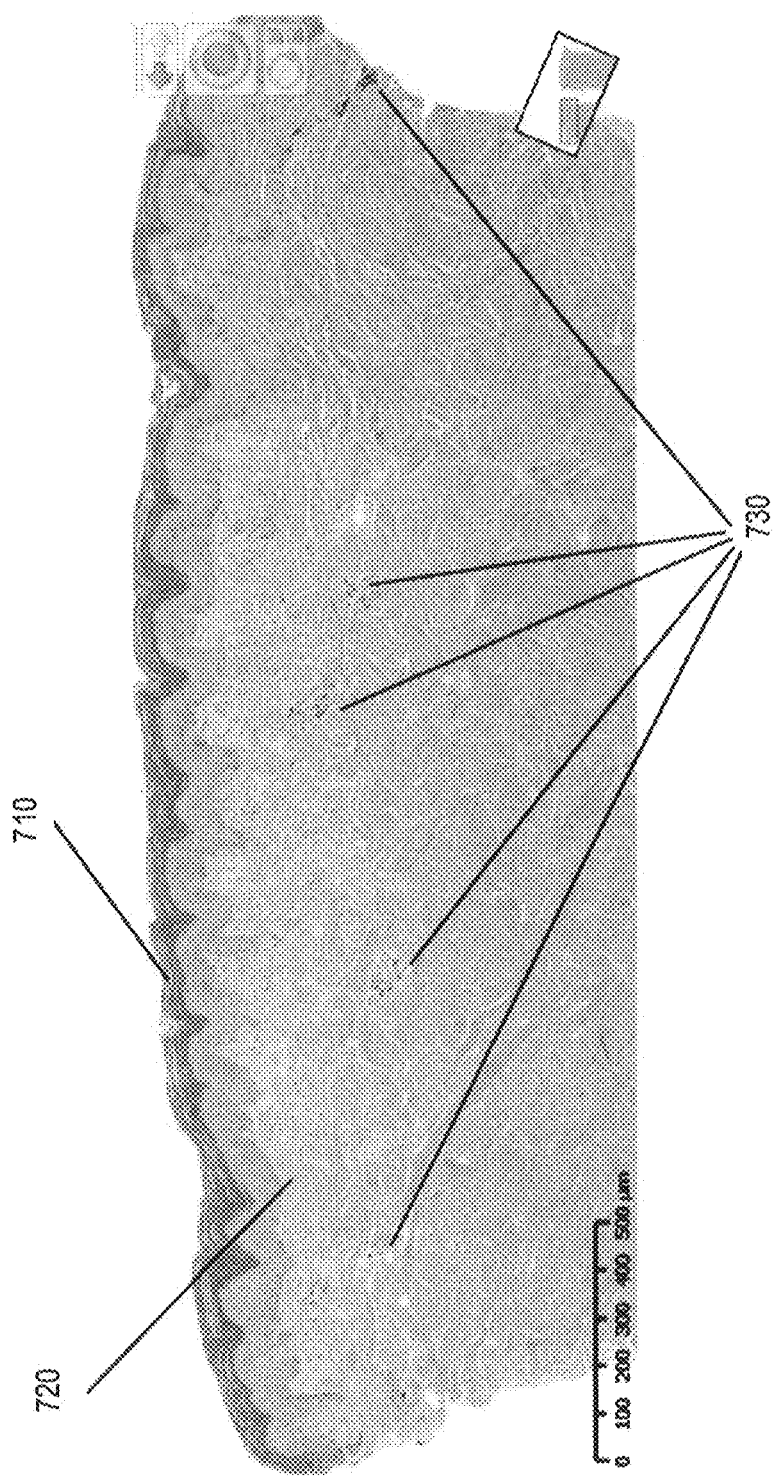
FIG. 7 illustrates an exemplary histology of a section of the melanin tattoo before treatment.

The treatment systems and methods described in this application can be used to selectively generating plasma in certain portions of a skin sample (e.g., porcine skin having a synthetic melanin tattoo, a carbon tattoo, etc.). The melanin tattoo can be located approximately between a quarter of a millimeter and a millimeter deep in the dermis of the skin sample. FIG. 7 illustrates an exemplary histology of a section of the melanin tattoo before treatment. A skin surface 710 is shown at the top of the histology. An epidermis-dermis junction, 720, demarcates the epidermis and dermis layers of the skin. Melanin globules 730 present in the dermis constitute the melanin tattoo. It can be seen from FIG. 7 that the epidermis contain native melanin and that the skin has a darker skin type (Fitzgerald skin type III).

Figure 8:
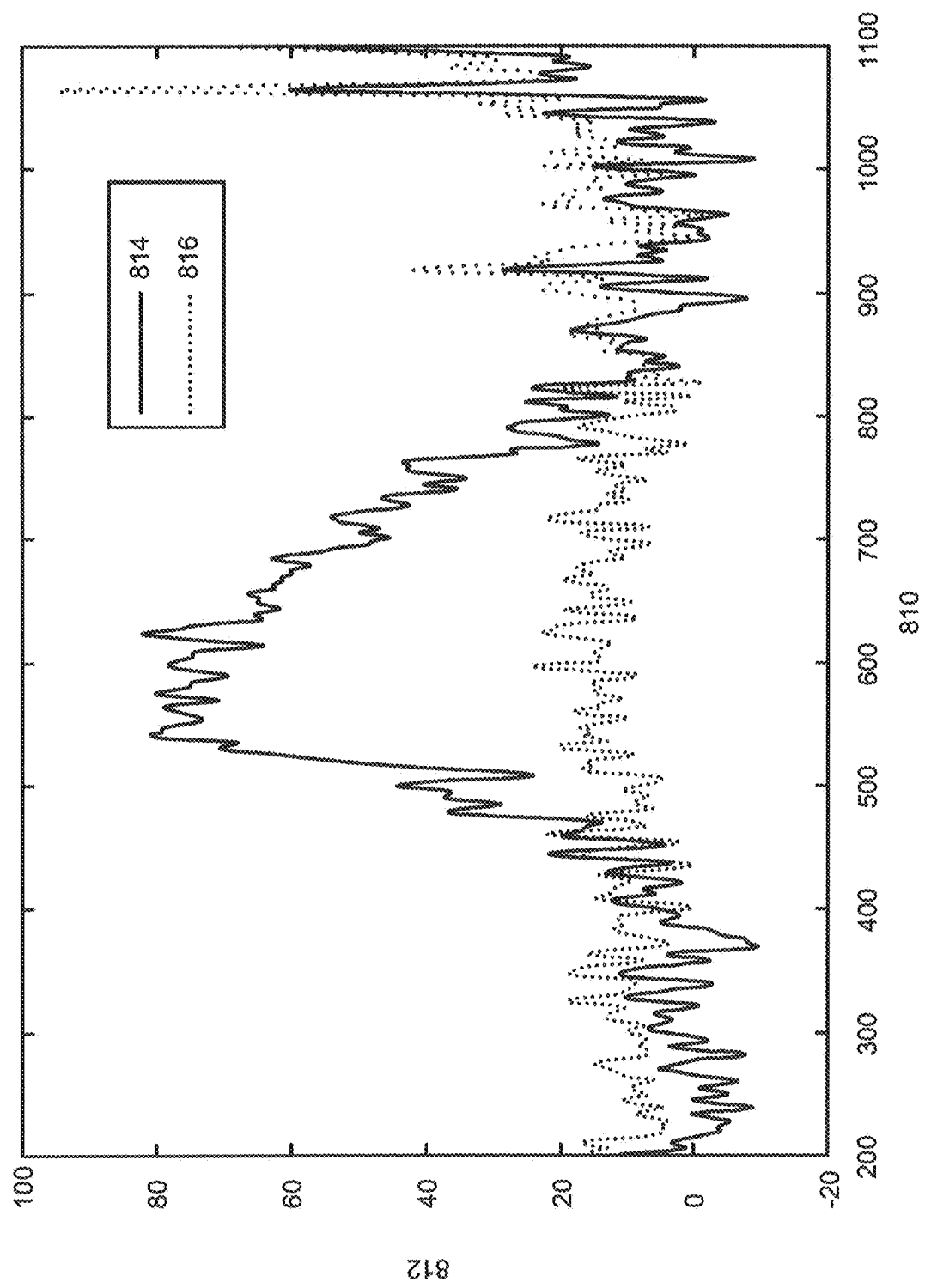
FIG. 8 illustrates an exemplary spectra measurement of a skin sample having melanin tattoo.

FIG. 8 illustrates an exemplary spectra measurement of a skin sample having melanin tattoo. Presence of visible light (having wavelength of about 400 nm to about 800 nm) in the skin sample spectra is indicative of plasma generation in the sample (e.g., skin sample 618). Wavelength in nanometers is shown along a horizontal axis 810. Relative intensity is shown along a vertical axis 812. Melanin tattoo spectrum 814 and a bare skin spectrum 816 are illustrated in FIG. 8. The melanin tattoo spectrum 814 shows a spectrum measurement taken during irradiation of a portion of the skin sample including melanin tattoo, and the bare skin spectrum 816 shows a spectrum measurement taken during irradiation of a portion of the skin sample that does not include the melanin tattoo ("bare skin"). The melanin tattoo spectrum 814 is indicative of the presence of a broad-spectrum light centered at about 600 nm and covering the visible spectrum. The bare skin spectrum 816 does not include radiation in the visible spectrum.

Figure 9:
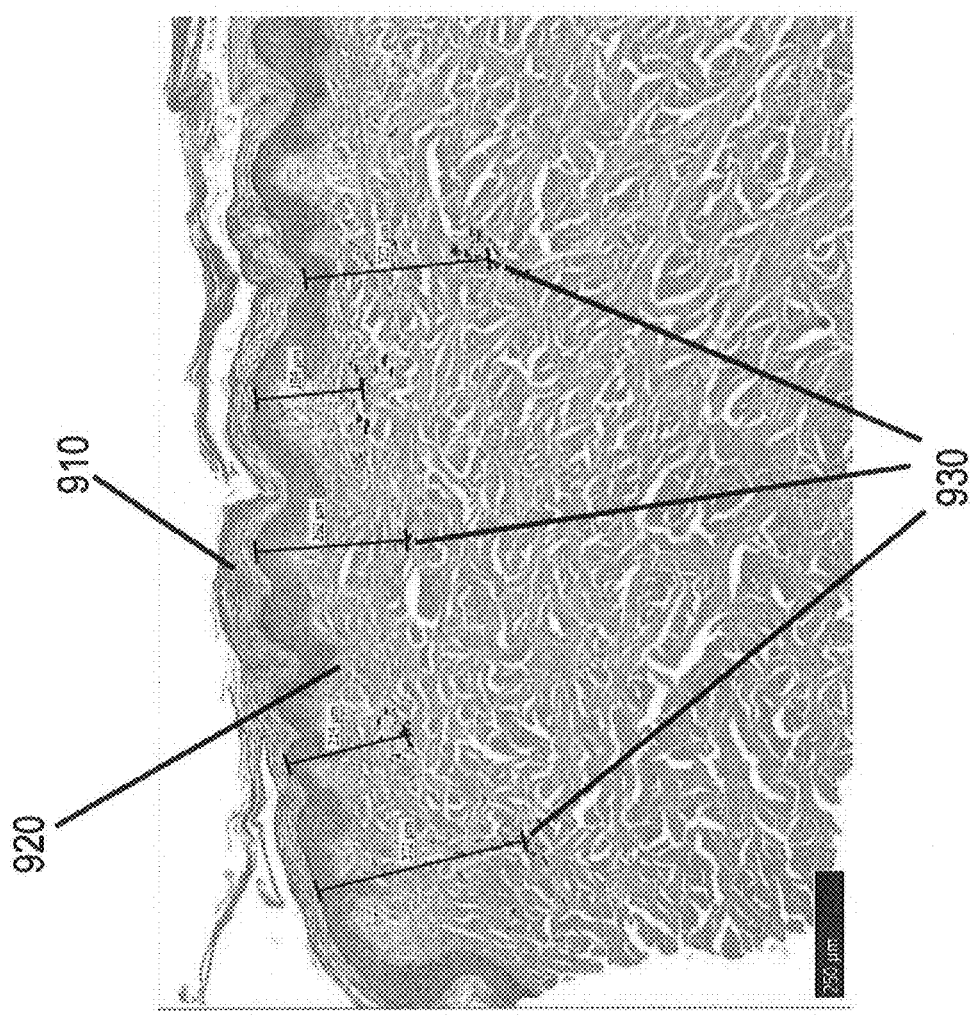
FIG. 9 illustrates an exemplary histology of a section of the carbon tattoo before treatment.

The carbon tattoo can be located approximately between a quarter of a millimeter and a millimeter deep in the dermis of the skin sample. FIG. 9 illustrates an exemplary histology of a section of the carbon tattoo before treatment. A skin surface 910 is shown at the top of the histology. An epidermis-dermis junction, 920, demarcates the epidermis and dermis layers of the skin. Carbon globules 930 present in the dermis constitute the melanin tattoo. It can be seen from FIG. 9 that the epidermis contains native melanin and that the skin has a darker skin type (Fitzgerald skin type III).

Figure 10:
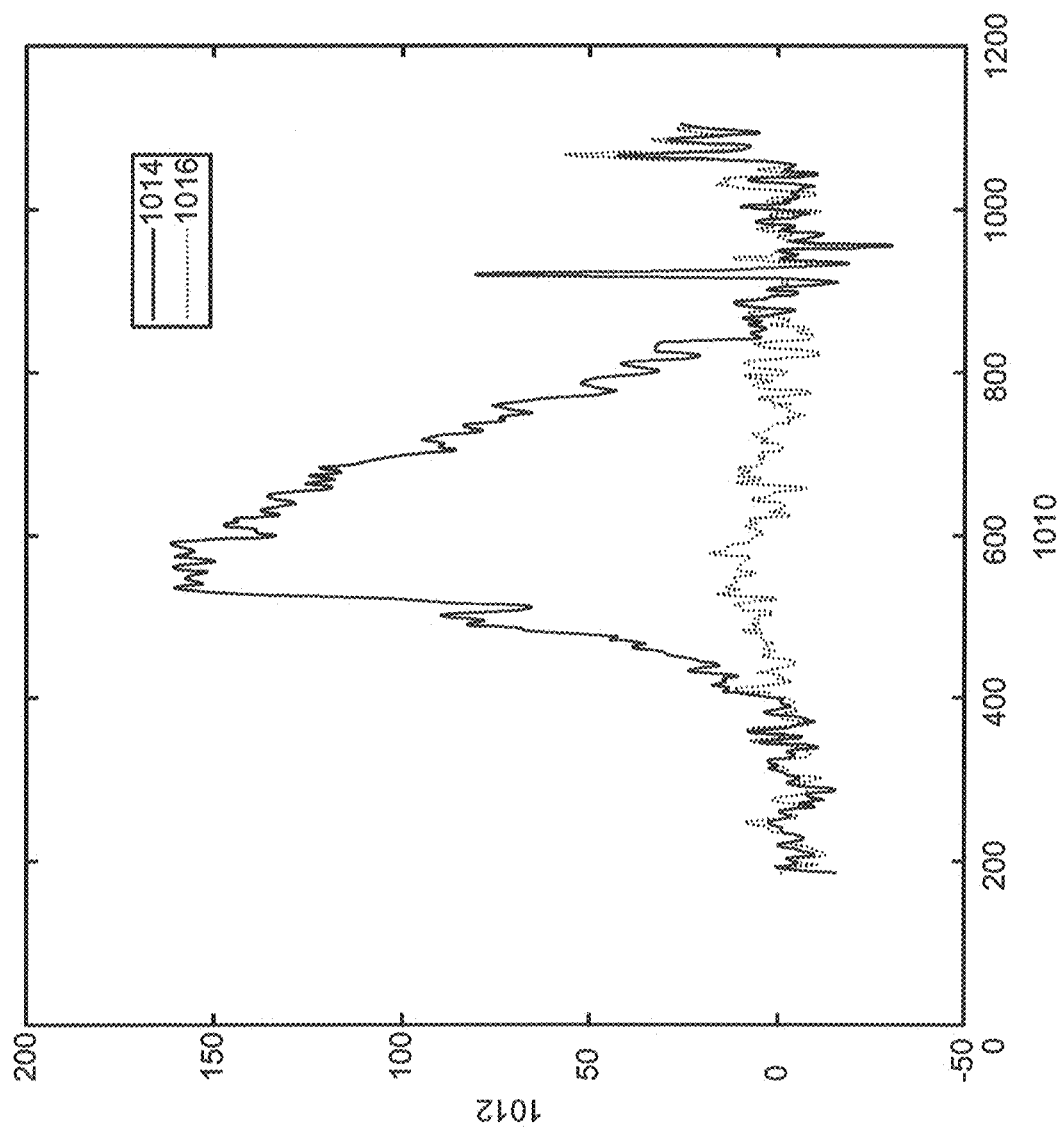
FIG. 10 illustrates an exemplary spectra measurement of a skin sample having carbon tattoo.

FIG. 10 illustrates an exemplary spectra measurement of a skin sample having carbon tattoo. Presence of visible light (having wavelength of about 400 nm to about 800 nm) in the skin sample spectra is indicative of plasma generation in the sample (e.g., skin sample 618). Wavelength in nanometers is shown along a horizontal axis 1010. Relative intensity is shown along a vertical axis 1012. Carbon tattoo spectrum 1014 and a bare skin spectrum 1016 are illustrated in FIG. 10. The carbon tattoo spectrum 1014 shows a spectrum measurement taken during irradiation of a portion of the skin sample including carbon tattoo, and the bare skin spectrum 1016 shows a spectrum measurement taken during irradiation of a portion of the skin sample that does not include the carbon tattoo ("bare skin"). The carbon tattoo spectrum 1014 is indicative of the presence of a broad-spectrum light centered at about 600 nm and covering the visible spectrum. The bare skin spectrum 1016 does not include radiation in the visible spectrum.

Figure 11:
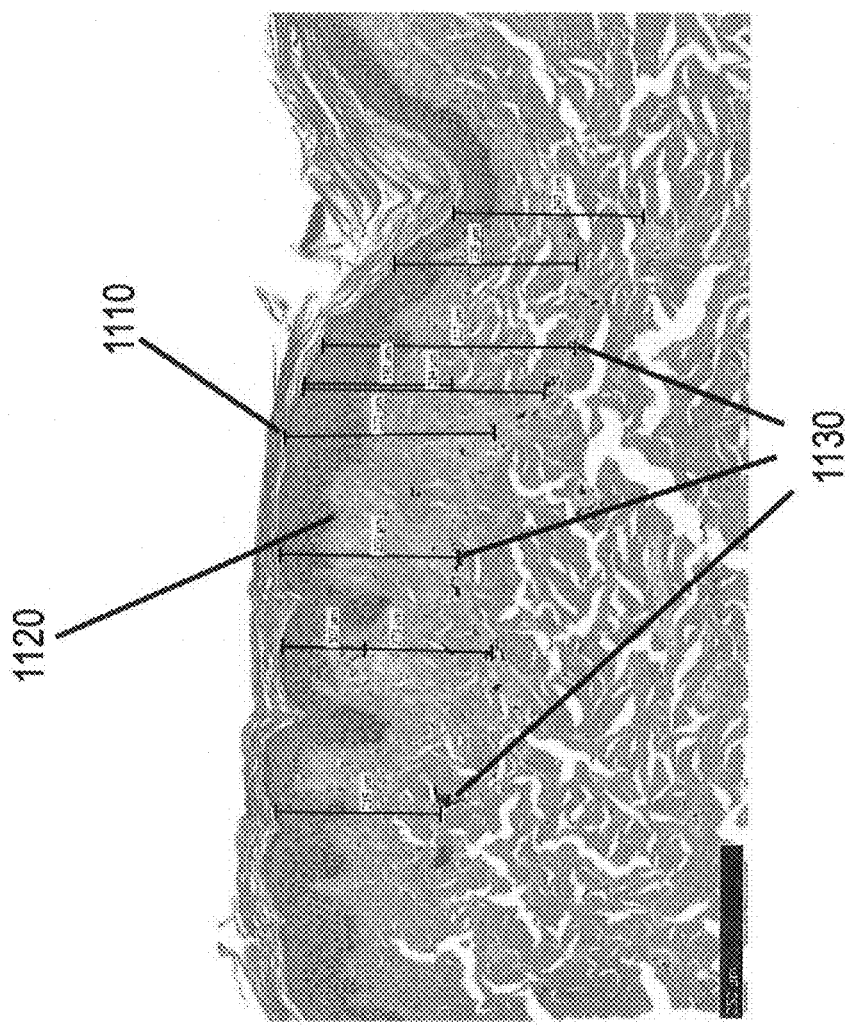
FIG. 11 illustrates an exemplary histology of a section of the carbon tattoo after treatment.

A histology of a section of the carbon tattoo after treatment is shown in FIG. 11. A skin surface, 1110, is shown at the top of the histology. An epidermis-dermis junction, 1120, demarcates the epidermis and dermis layers of the skin. carbon globules, 1130, present in the dermis constitute the carbon tattoo. It can be seen from FIG. 11 that the carbon globules 1130 have been disrupted. Distances 1140 between the skin surface 1110 and the carbon globules 1130 are shown below.

As the proof of concept above indicates, a focused beam can be used to selectively initiate a plasma within a dopant at a prescribed depth within a pigmented tissue. A laser beam directed to a focal region beneath a carbon rich epidermis can selectively initiate a plasma only in the dermal pigment, while initiating no plasma in the above epidermis.

Figure 12:
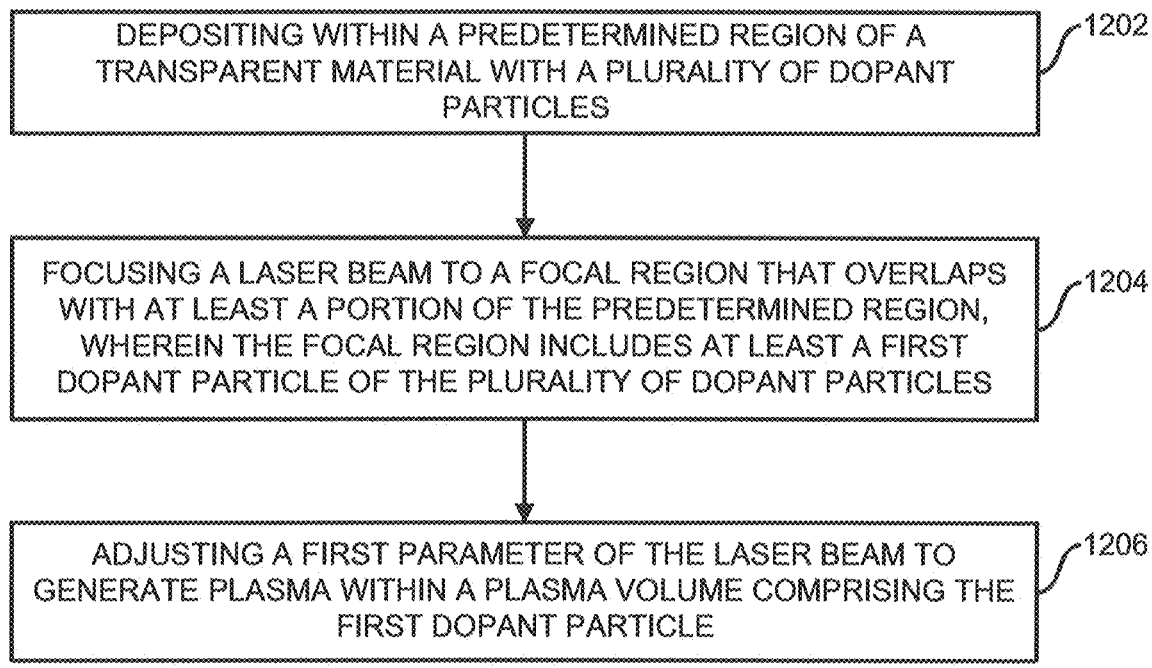
FIG. 12 is a flow diagram illustrating one exemplary embodiment of a method for selective plasma generation in a target tissue.

FIG. 12 is a flow diagram illustrating one exemplary embodiment of a method for selective plasma generation in a target tissue. At 1202, a plurality of dopant particles are deposited in a predetermined region of the target tissue. The predetermined region can correspond to the portion where the target tissue that needs to be treated. At 1204, a laser beam (e.g., focused laser beam 506) is focused to a focal region (e.g., focal region 508) that overlaps with at least a portion of the predetermined region (e.g., doped region 512). The focal region includes at least a first dopant particle of the plurality of dopant particles. For example, the focal region can overlap with a dopant particle (e.g. dopant particle 516). The focal region of the laser beam can correspond to a region where the intensity of the laser beam is above a threshold value (e.g., portion of the laser beam in the Rayleigh range). At 1206, a first parameter of the laser beam (e.g., intensity, wavelength, power, pulse energy) can be adjusted to generate plasma within a plasma volume comprising the first dopant particle. The plasma volume can be, for example, a volume surrounding a dopant particle (e.g., dopant particle 516).

Example 1

Doping of tissue according to some embodiments is shown by way of a hair follicle doping example. In order to dope pigmentless hair follicles, an example hair follicle doping procedure was followed. The follicle doping procedure is intended to open up hair follicles and remove excess lipids, so that a hydrogenous dye may penetrate the hair follicles and not penetrate or stain the outer layer of skin. The hair follicles are more hydrophilic than the outer layer of skin or stratum corneum, which is generally lipophilic. Skin from a white Yorkshire pig was used for the example.

Figure 13:
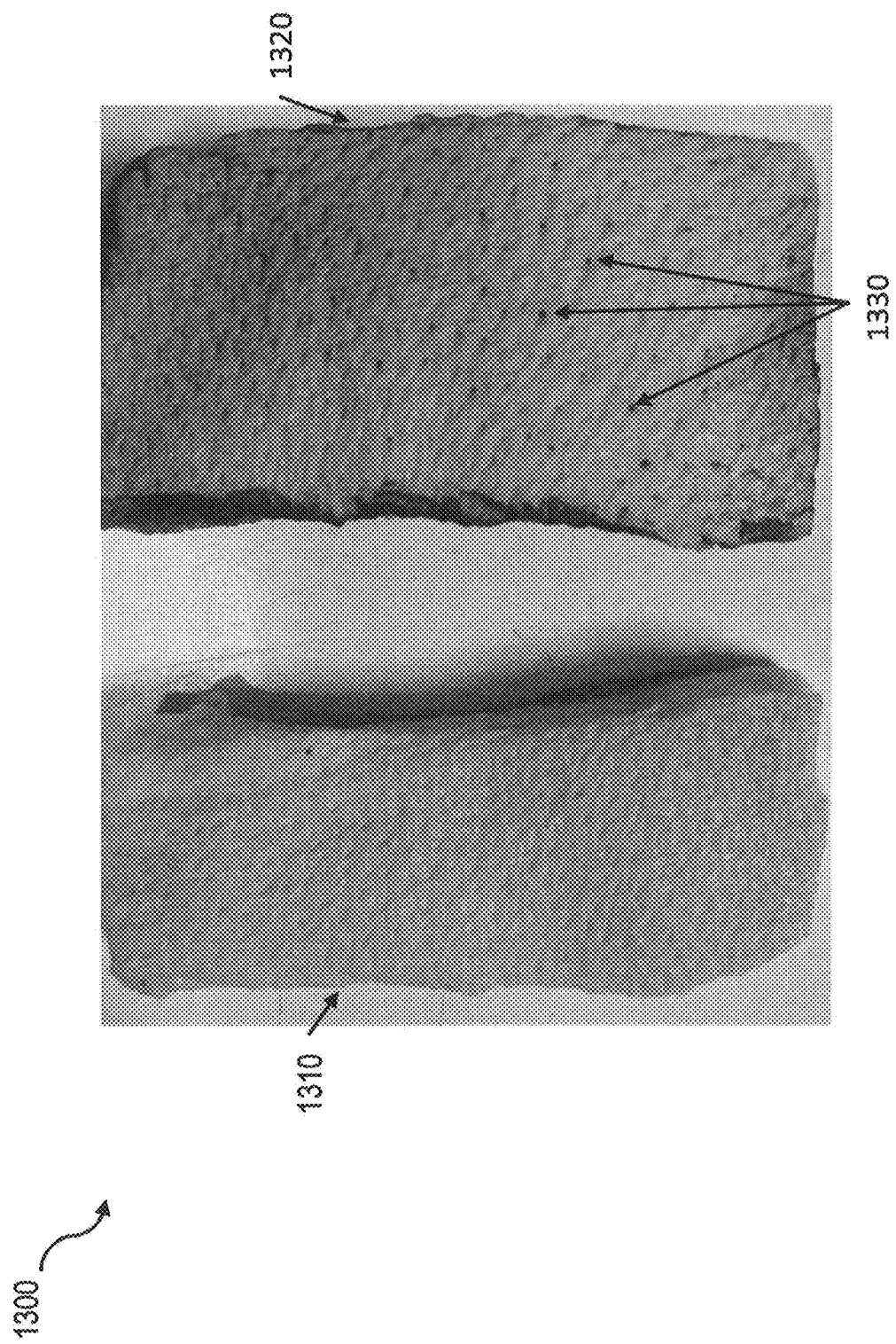
FIG. 13 is an image showing an undoped sample and a doped sample of a white pig skin, according to some embodiments.
Figure 14:
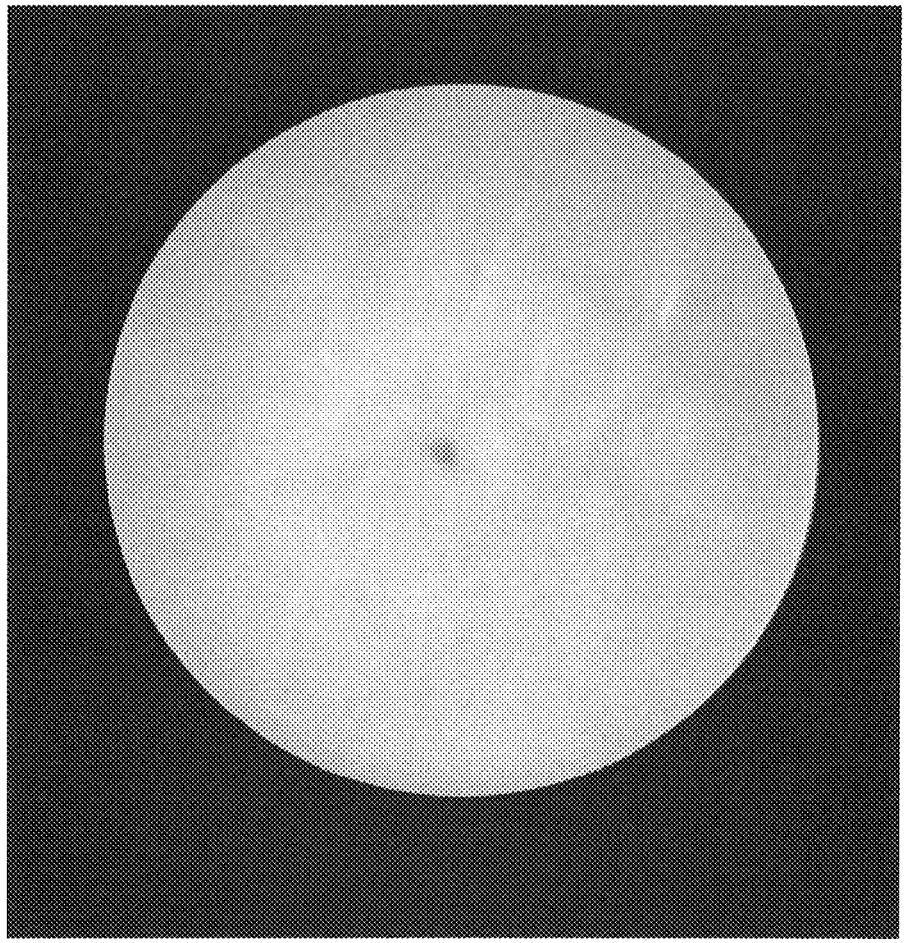
FIG. 14 is an exemplary magnified image of a hair follicle of a control sample, according to some embodiments.
Figure 15:
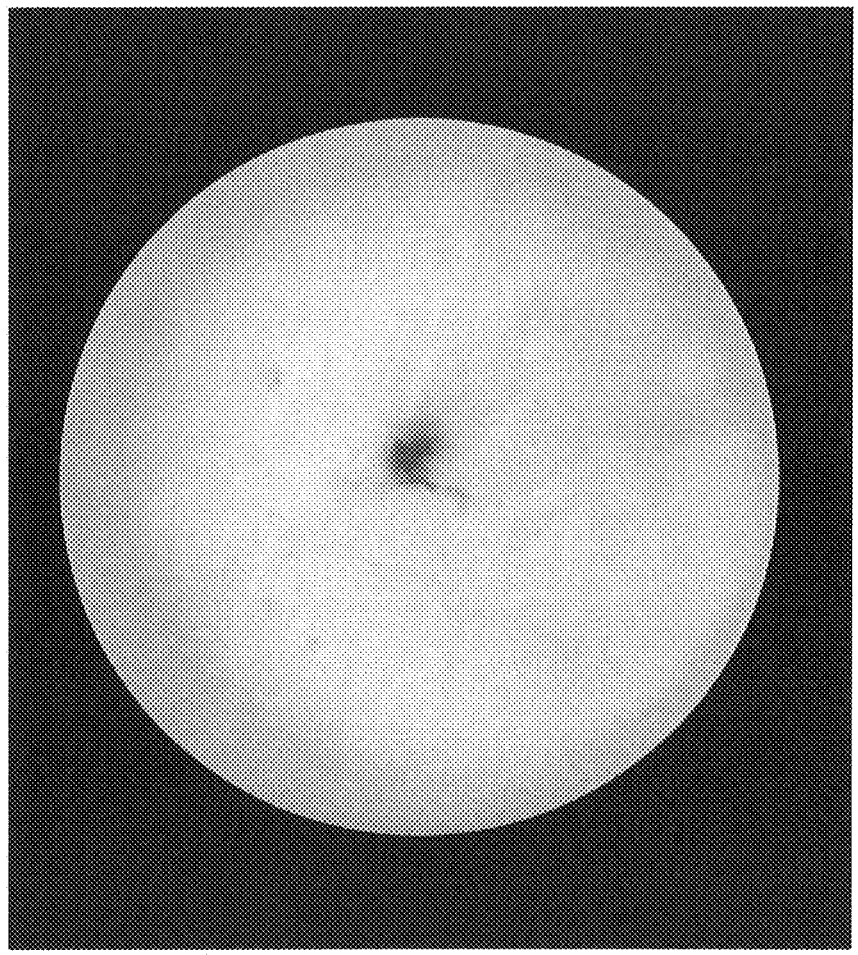
FIG. 15 is an exemplary magnified image of a hair follicle of a doped sample, according to some embodiments.

Hairs on the skin were removed by waxing in preparation of doping. The wax used was from a Sally Hansen Extra Strength All-Over Body Wax Kit distributed by Coty US LLC of New York, N.Y. Residual wax was removed with solvent also from the waxing kit. Pores on the skin were further evacuated through use of Deep Cleansing Pore Strips from Bioré distributed by Kao USA Inc. of Cincinnati, Ohio. The skin was then degreased with rubbing alcohol. The skin was bisected into two samples. Referring to FIG. 13, an image 1300 of the skin samples is shown. A first sample was left as a control sample 1310. And, a second sample was doped becoming a doped sample 1320. A dye was prepared for doping. The dye comprised water and a water soluble near-IR pigment having peak absorption at about 1054 nm (Part No. NIR1054B from QCR Solutions of Port Lucie, Fla.). The dye was applied to a top surface of the skin of the doped sample 1320 with a brush. With the top skin surface coated in dye, the doped sample was massaged using a percussion massager. After massaging the doped sample, both the control sample and the doped sample were wiped clean. It can be seen from FIG. 13 that the doped sample 1320, contains visible pigment in and about doped hair follicles 1330 where the control sample does not. In FIG. 14, an image 1400 is shown of an undoped hair follicle from the control sample under magnification. In FIG. 15, an image 1500 is shown of a doped hair follicle from the doped sample under magnification.

Example 2

Tests have been performed to show that transmissive materials having different ionization energies may be used to lower the threshold LIOB intensity. A number of optical windows have been selected. The different optical windows are made of different materials: NaCl, KBr, Sapphire, and Fused Silica. A Q-Switched Nd:Yag laser (Quantel Q-Smart 450) is used along with an optical chain to deliver a focused laser pulse at each window sample. Neutral density (ND) filters are used to attenuate the laser and Q-Switch delay is used to vary the amount of energy delivered by each laser pulse. The laser is attenuated with ND filters having a cumulative OD of 3.6. The laser beam is focused using an 8 mm EFL lens (Thorlabs Part No. C240TME-C). For the purposes of estimating irradiance, the focused spot size is assumed to be 10 µm ($1/e^2$) diameter for all materials. This assumption is based upon previous measurements of the spot size using this lens, which yielded a 7 µm ($1/e^2$) diameter measurement in air. A minimum amount of energy needed to induce a plasma in each window is discovered by varying the pulse energy low enough until no plasma is formed and then increasing the pulse energy until a plasma is first observed. Results from the tests are shown in the table below:

| Material | Edmunds Optic Part No. | Q-Switch Delay (uS) | Estimated Peak Power (KW) | Estimated Peak Irradiance (GW/cm²) | Percentage of Max. Material Threshold (%) |
|---|---|---|---|---|---|
| Fused Silica | 45-311 | 80 | 6.5183888 | 8.2994704 | 100% |
| Sapphire | 48-919 | 90 | 5.6806368 | 7.2328114 | 87% |
| NaCl | 68-817 | 140 | 1.45696 | 1.8550591 | 22% |
| KBr | 68-809 | 160 | 0.8792 | 1.1194322 | 13% |

It can be seen that the minimum energy needed to induce breakdown in each material is not constant. Materials containing electron donors (NaCl, KBr) breakdown with less energy and are therefore suitable dopants to lower the LIOB threshold of a material. As these materials are all transmissive at the laser wavelength (1064 nm) it is believed that breakdown is photon induced rather than thermionic.

Example 3

Figure 16:
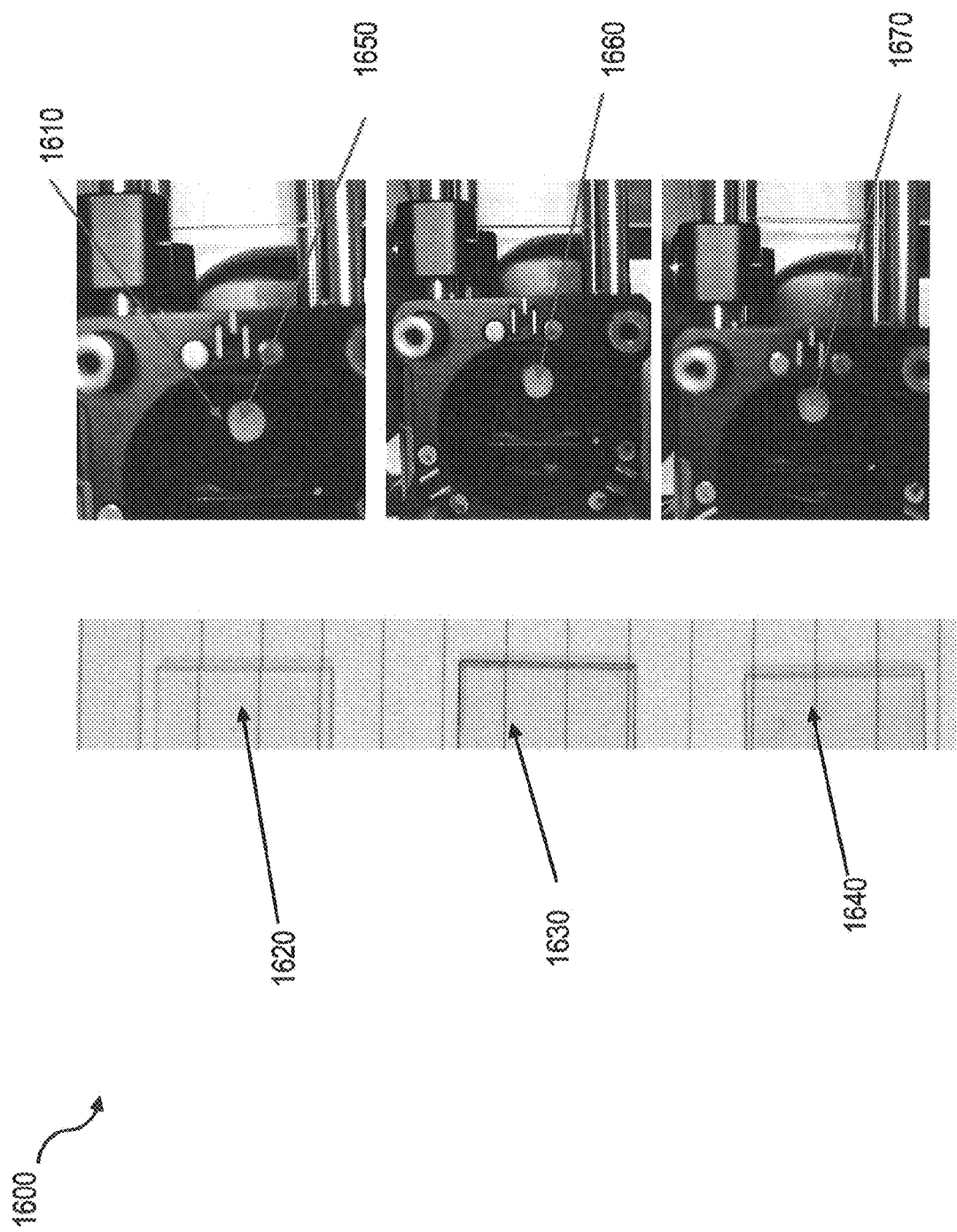
FIG. 16 is a series of exemplary images showing effects of near infrared absorbing pigments (i.e., dopants) on visible and near infrared light, according to some embodiments.

According to some embodiments a generally absorbing material is added as a dopant to aid in LITB. Referring to FIG. 16, a series of images 1600 show absorbing pigments and their effect on a 1060 nm laser beam. An 8 mm diameter 1060 nm laser beam was deliver to a fluorescing disk 1610 that fluoresces green when near IR radiation is applied. Three slides were prepared, one slide contained water 1620, one contained NIR1031M pigment in acetone 1630, and one contained NIR1054B in water 1640. It can be seen from the images 1600 that the pigment containing slides only slightly affected transmission of visible light. When the water 1620 was placed in the laser beam path an intensity of the laser beam passing through water 1650 (as indicated by the fluorescing disk 1610) was generally unaffected. When the NIR1031M slide 1630 was placed in the laser beam path an intensity of the laser beam passing through NIR1031M 1660 was reduced. Likewise, when the NIR1054B slide 1640 was placed in the laser beam path, an intensity of the laser beam passing through the NIR1054B was almost fully attenuated. It is therefore shown that a pigment have peak absorption about a laser wavelength may absorb the laser beam intensity and not drastically affect the visible (e.g., transparent properties of a material). In order to further summarize, a table is presented below thank includes parameter ranges for some exemplary embodiments.

| | Min. | Nom. | Max. |
|---|---|---|---|
| Numerical Aperture | 0.01 | 0.5 | 1 |
| Wavelength (nm) | 200 | 1060 | 20,000 |
| Rep. Rate (Hz) | 10 | 10,000 | 200,000 |
| Pulse Duration (nS) | $1 \times 10^{-4}$ | 100 | $1 \times 10^5$ |
| $M^2$ | 1 | 1.5 | 3 |
| Material | Materials that a generaly transparent in a range of EMR (e.g., visible range, UV range, and/or near IR range), for example: Thermoplastics, such as PMMA, HEMA and polycarbonate; other polymers; glass; and crystal (e.g., quartz). | | |
| Concentration | A concentration of at least as great as one dopant particle per focal volume, for example in a range of between 0.00001 mg/ml and 10 g/ml | | |
| LITB Dopant | Materials being generally absorbing at an EMR wavelength, for example: carbon, melanin, absorbing pigments and dyes (e.g., India ink), metal nanoparticles, and dendritic molecules. Materials and methods to alter a pH or oxygen concentration. | | |
| LIOB Dopant | Materials containing an element having a low ionization energy, such as: Sodium, Potassium, and many non-metals; low band gap dielectrics such as: Aluminum gallium arsenide, Zinc oxide doped with aluminum, indium or gallium, and Gallium phosphate; materials with a low local work function, such as: nanoparticles having a surface area lowering the local work function of the material below that of a bulk work function. Materials and methods to alter a pH or oxygen concentration. | | |

Additionally, Oxygen concentration and/or pH may alter the plasma threshold in tissues. Therefore, according to some embodiments, pH and/or Oxygen concentration within a tissue is altered in order to change a laser induced breakdown threshold within the tissue. Dopants may be used which alter pH and/or oxygen concentration. Additionally, biological responses which induce a change in pH and/or oxygen concentration may be initiated. For example, inflammation is known to alter the pH within a tissue as is exercise (from lactic acid). The material may then be irradiated at a different laser induced breakdown threshold in order to realize a selective treatment. Oxygen concentration can vary from cell to cell. Therefore according to some embodiments, cells may be selectively treated (through plasma mediated treatment).

Methods of treating various skin conditions, such as for cosmetic purposes, can be carried out using the systems described herein. It is understood that although such methods can be conducted by a physician, non-physicians, such as aestheticians and other suitably trained personnel may use the systems described herein to treat various skin conditions with and without the supervision of a physician.

Additional Embodiments

In some embodiments, the repetition rate of the input laser beam can be faster than the decay rate of the plasma in the target tissue/target material. This can allow for continuous (e.g., temporally continuous, spatially continuous, etc.) generation of plasma. The area of the treatment region/target region (e.g., region in which plasma is generated) can be controlled by changing the repetition rate of the laser beam.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

Approximating language, as used herein throughout the specification and claims, may be applied to modify any quantitative representation that could permissibly vary without resulting in a change in the basic function to which it is related. "Approximately," "substantially, or "about" can include numbers that fall within a range of 1%, or in some embodiments within a range of 5% of a number, or in some embodiments within a range of 10% of a number in either direction (greater than or less than the number) unless otherwise stated or otherwise evident from the context (except where such number would impermissibly exceed 100% of a possible value). Accordingly, a value modified by a term or terms, such as "about," approximately, or "substantially," is not to be limited to the precise value specified. In at least some instances, the approximating language may correspond to the precision of an instrument for measuring the value. Here and throughout the specification and claims, range limitations may be combined and/or interchanged, such ranges are identified and include all the sub-ranges contained therein unless context or language indicates otherwise.

The articles "a" and "an" as used herein in the specification and in the claims, unless clearly indicated to the contrary, should be understood to include the plural referents. Claims or descriptions that include "or" between one or more members of a group are considered satisfied if one, more than one, or all of the group members are present in, employed in, or otherwise relevant to a given product or process unless indicated to the contrary or otherwise evident from the context. The disclosure includes embodiments in which exactly one member of the group is present in, employed in, or otherwise relevant to a given product or process. The disclosure also includes embodiments in which more than one, or all of the group members are present in, employed in, or otherwise relevant to a given product or process. Furthermore, it is to be understood that the disclosed embodiments provide all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. It is contemplated that all embodiments described herein are applicable to all different aspects of the disclosed embodiments where appropriate. It is also contemplated that any of the embodiments or aspects can be freely combined with one or more other such embodiments or aspects whenever appropriate. Where elements are presented as lists, e.g., in Markush group or similar format, it is to be understood that each subgroup of the elements is also disclosed, and any element(s) can be removed from the group. It should be understood that, in general, where the disclosed embodiments, or aspects of the disclosed embodiments, is/are referred to as comprising particular elements, features, etc., certain embodiments of the disclosure or aspects of the disclosure consist, or consist essentially of, such elements, features, etc. For purposes of simplicity those embodiments have not in every case been specifically set forth in so many words herein. It should also be understood that any embodiment or aspect of the disclosure can be explicitly excluded from the claims, regardless of whether the specific exclusion is recited in the specification. For example, any one or more active agents, additives, ingredients, optional agents, types of organism, disorders, subjects, or combinations thereof, can be excluded.

Where ranges are given herein, embodiments of the disclosure include embodiments in which the endpoints are included, embodiments in which both endpoints are excluded, and embodiments in which one endpoint is included and the other is excluded. It should be assumed that both endpoints are included unless indicated otherwise. Furthermore, it is to be understood that unless otherwise indicated or otherwise evident from the context and understanding of one of ordinary skill in the art, values that are expressed as ranges can assume any specific value or subrange within the stated ranges in different embodiments of the disclosure, to the tenth of the unit of the lower limit of the range, unless the context clearly dictates otherwise. It is also understood that where a series of numerical values is stated herein, the disclosure includes embodiments that relate analogously to any intervening value or range defined by any two values in the series, and that the lowest value may be taken as a minimum and the greatest value may be taken as a maximum. Numerical values, as used herein, include values expressed as percentages.

Any embodiment in which a numerical value is prefaced by "about" or "approximately" includes an embodiment in which the exact value is recited. For any embodiment of the disclosure in which a numerical value is not prefaced by "about" or "approximately", the disclosure includes an embodiment in which the value is prefaced by "about" or "approximately." "Approximately" or "about" can include numbers that fall within a range of 1% or in some embodiments within a range of 5% of a number or in some embodiments within a range of 10% of a number in either direction (greater than or less than the number) unless otherwise stated or otherwise evident from the context (except where such number would impermissibly exceed 100% of a possible value).

It should be understood that, unless clearly indicated to the contrary, in any methods claimed herein that include more than one act, the order of the acts of the method is not necessarily limited to the order in which the acts of the method are recited, but the disclosure includes embodiments in which the order is so limited. It should also be understood that unless otherwise indicated or evident from the context, any product or composition described herein may be considered "isolated."

As used herein the term "comprising" or "comprises" is used in reference to compositions, methods, and respective component(s) thereof, that are essential to the disclosed embodiments, yet open to the inclusion of unspecified elements, whether essential or not.

As used herein the term "consisting essentially of" refers to those elements required for a given embodiment. The term permits the presence of additional elements that do not materially affect the basic and novel or functional characteristic(s) of that embodiment of the disclosure.

The term "consisting of" refers to compositions, methods, and respective components thereof as described herein, which are exclusive of any element not recited in that description of the embodiment.

Although a few variations have been described in detail above, other modifications or additions are possible.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." In addition, use of the term "based on," above and in the claims is intended to mean, "based at least in part on," such that an unrecited feature or element is also permissible.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and sub-combinations of the disclosed features and/or combinations and sub-combinations of several further features disclosed above. In addition, the logic flows depicted in the accompanying figures and/or described herein do not necessarily require the particular order shown, or sequential order, to achieve desirable results. Other implementations may be within the scope of the following claims.

What is claimed is:

1. A method comprising:
   depositing within a predetermined region of a target tissue with a plurality of dopant particles;
   focusing a laser beam to a focal region that overlaps with at least a portion of the predetermined region, wherein the focal region includes at least a first dopant particle of the plurality of dopant particles;
   adjusting a first parameter of the laser beam comprising at least a maximum intensity to generate plasma within a plasma volume comprising the first dopant particle, wherein the maximum intensity is between a threshold value of the target tissue without the dopant particles and a threshold value of the target tissue with the dopant particles; and
   scanning the focal region of the laser beam along a first path in the predetermined region;
   wherein scanning the focal region along the first path is configured to one or more of destroy, obliterate, cavitate, ablate, denature, and devitalize the target issue along the first path.

2. The method of claim 1, wherein the plasma is generated within the first dopant particle.

3. The method of claim 1, wherein the plasma is generated in the plasma volume via laser induced thermal breakdown (LITB) due to absorption of a portion of the laser beam by the first dopant particle.

4. The method of claim 3, wherein the maximum intensity of the laser beam in the focal region is below a LITB threshold value of the target tissue without the dopant particles.

5. The method of claim 4, wherein adjusting the first parameter of the laser beam comprises setting the maximum intensity of the laser beam to a value between the LITB threshold value of the target tissue without the dopant particles and the LITB threshold value of the target tissue with the dopant particles.

6. The method of claim 1, wherein the plasma is generated in the plasma volume via laser induced optical breakdown (LIOB) due to absorption of a portion of the laser beam by the first dopant particle.

7. The method of claim 6, wherein the maximum intensity of the laser beam in the focal region is below a LITB threshold value of the target tissue without the dopant particles.

8. The method of claim 7, wherein adjusting the first parameter of the laser beam comprises setting the maximum intensity of the laser beam to a value between the LITB threshold value of the target tissue without the dopant particles and the LITB threshold value of the target tissue with the dopant particles.

9. The method of claim 1, wherein adjusting the first parameter of the laser beam comprises adjusting one or more of a power, a pulse energy, and a wavelength of the laser beam.

10. The method of claim 1, wherein the plurality of dopant particle includes one or more of sodium chloride, silicon, silver nanoparticles, metal nanocomposites, dendritic molecules.

11. The method of claim 1, wherein the generated plasma includes a first plasma generated from the first dopant particle, and a second plasma generated from the target tissue.

12. The method of claim 1, wherein the plurality of dopant particle are deposited in the predetermined region by at least injecting the plurality of dopant particles in the target tissue.

13. The method of claim 1, wherein the laser beam is focused by a lens having a numerical aperture of at least 0.3.

14. The method of claim 1, wherein the laser beam has a wavelength selected based upon at least one of scattering and absorption in the target tissue.

15. The method of claim 14, wherein the wavelength is between 0.5 and 2.0 micron.

16. The method of claim 1, wherein the plurality dopant particles are nanoparticles.

* * * * *